(12) United States Patent
El Fathi et al.

(10) Patent No.: US 11,931,548 B2
(45) Date of Patent: Mar. 19, 2024

(54) METHOD AND SYSTEM FOR DETERMINING OPTIMAL AND RECOMMENDED THERAPY PARAMETERS FOR DIABETIC SUBJECT

(71) Applicants: Anas El Fathi, Lasalle (CA); Ahmad Haidar, Montreal (CA); Robert Edward Kearney, Montreal (CA)

(72) Inventors: Anas El Fathi, Lasalle (CA); Ahmad Haidar, Montreal (CA); Robert Edward Kearney, Montreal (CA)

(73) Assignees: Anas El Fathi, Lasalle (CA); Ahmad Mohamad Haidar, Montreal (CA); Robert Edward Kearney, Montreal (CA)

( * ) Notice: Subject to any disclaimer, the term of this patent is extended or adjusted under 35 U.S.C. 154(b) by 584 days.

(21) Appl. No.: 17/003,553

(22) Filed: Aug. 26, 2020

(65) Prior Publication Data
US 2022/0062544 A1 Mar. 3, 2022

(51) Int. Cl.
*A61M 5/172* (2006.01)
*G16H 20/17* (2018.01)
*G16H 20/60* (2018.01)

(52) U.S. Cl.
CPC .......... *A61M 5/1723* (2013.01); *G16H 20/17* (2018.01); *G16H 20/60* (2018.01);
(Continued)

(58) Field of Classification Search
CPC .......... A61M 5/1723; A61M 2230/201; A61M 2205/50; A61M 2205/3303; G16H 20/60; G16H 20/17
See application file for complete search history.

(56) References Cited

U.S. PATENT DOCUMENTS

2019/0214124 A1 7/2019 Mougiakakou et al.
2020/0016336 A1* 1/2020 Patek ................ A61M 5/14244

FOREIGN PATENT DOCUMENTS

EP 2456351 B1 10/2016
EP 2350895 B1 6/2019
(Continued)

OTHER PUBLICATIONS

Mitra and Hlavacek, Parameter estimation and uncertainty quantification for systems biology models, 18 Current Opinion in Systems Biology 9-18 (Nov 6, 3019) (Year: 2019).*
(Continued)

*Primary Examiner* — Evangeline Barr
*Assistant Examiner* — Jordan L Jackson
(74) *Attorney, Agent, or Firm* — Fasken Martineau DuMoulin, LLP; Serge Lapointe

(57) ABSTRACT

There is provided a method and a system for determining recommended multiple daily injections (MDI) therapy values for administering to a given subject. Consumed meals, insulin basal doses administered and insulin bolus doses administered to the given subject are received. An initial meal ratio parameter and an initial basal insulin dose used by the given subject are received. A predicted glucose concentration parameter is determined based on the consumed meals, the insulin basal dose, the insulin bolus doses, and the initial meal ratio parameter. An actual glucose concentration parameter is received. A set of optimal MDI therapy parameters are estimated using the predicted glucose concentration parameter, and the actual glucose concentration parameter. A set of optimal MDI therapy parameters are determined based on the current MDI therapy parameters, the set of recommended MDI therapy parameters comprising an optimal meal ratio parameter, and an optimal basal insulin dose to be administered to the given subject.

20 Claims, 8 Drawing Sheets

(52) U.S. Cl.
CPC . *A61M 2205/3303* (2013.01); *A61M 2205/50* (2013.01); *A61M 2230/201* (2013.01)

(56) References Cited

FOREIGN PATENT DOCUMENTS

| WO | 2011039741 A1 | 4/2011 |
|----|---------------|--------|
| WO | 2018187539 A1 | 10/2018 |
| WO | 2019169007 A1 | 9/2019 |

OTHER PUBLICATIONS

Sarvesh Dwivedi, Bayesian parameter estimation for dynamical biological systems with adaptive sparse grids, Masters Thesis Eidgenössische Technische Hochschule Zürich, Department of Computer Science (Year: 2011).*

Sinha et al., Neural Bridge Sampling for Evaluating Safety-Critical Autonomous Systems, 34th Conference on Neural Information Processing Systems (Aug. 24, 2020) (Year: 2020).*

Magni et al., Run-to-Run Tuning of Model Predictive Control for Type 1 Diabetes Subjects: In Silico Trial, 3(5) J. Diabetes Sci. Tech. 1091-1098 (Sep. 2009) (Year: 2009).*

Sánchez et al., Parameter estimation of a meal glucose-insulin model for T1DM patients from therapy historical data, 13(1) IET Systems Bio 8-15 (Nov. 18, 2018) (Year: 2018).*

Cescon et al., Iterative Learning Control with Sparse Measurements for Long-Acting Insulin Injections in People with Type 1 Diabetes, 2019 American Control Conference (ACC) 4746-4751 (Jul. 2019) (Year: 2019).*

Publication: "A new Typology Design of Performance Metrics to Measure Errors in Machine Learning Regression Algorithms"—Botchkarev—Jan. 17, 2019—Interdisciplinary Journal of Information, Knowledge and Management, vol. 14, 2019—Retrieved on Nov. 23, 2021 http://www.ijikm.org/Volume14/IJIKMv14p045-076Botchkarev5064.pdf.

"Variability: Range, Mean Absolute Deviation, Variance, Standard Deviation, Coefficient of Variation" Nov. 2, 2015 https://youtube.com/watch?v=fvgDqVda9L8&t=860s.

* cited by examiner

METHOD AND SYSTEM FOR DETERMINING OPTIMAL AND RECOMMENDED THERAPY PARAMETERS FOR DIABETIC SUBJECT

CROSS-REFERENCE TO RELATED APPLICATIONS

None.

FIELD

The present technology relates to drug monitoring systems in general and more specifically to a method and a system for determining optimal and recommended multiple daily injection (MDI) therapy parameters for a diabetic subject.

BACKGROUND

Insulin is a hormone that is secreted by the pancreas to regulate blood glucose levels, and is absent in people with type 1 diabetes (T1D) due to the autoimmune destruction of the pancreatic beta cells. T1D is treated with a lifelong intensive insulin-replacement therapy using multiple daily injections (MDI) or continuous subcutaneous insulin infusion via a portable pump. Intensive insulin therapy is key to reducing long-term micro- and macrovascular complications caused by sustained high glucose levels (hyperglycemia). However, most people with T1D do not achieve acceptable glucose targets, as tight glycemic control is challenging due to fear of low glucose levels (hypoglycemia).

MDI therapy consists of a basal-bolus insulin regimen that aims to mimic insulin secretion patterns in healthy individuals. Basal insulin aims to maintain glucose levels constant during fasting and overnight, accounting for about 50% of a daily insulin requirements. Basal insulin is delivered in 1-2 doses/day of long- or intermediate-acting insulin; these insulins are characterized by a slow, often peak-less, absorption with a duration effect up to 24 hours. Basal insulin requirements may change depending on a person sleep cycle, physical activities, psychological stress, and growth hormones.

Bolus insulin refers to rapid-acting insulin doses given at mealtimes to metabolize meal-related glucose appearance in the blood. Insulin boluses are determined based on the carbohydrate ratios which specifies how many grams of carbohydrate are metabolized by each unit of insulin. Carbohydrate ratios change depending on the time of the day, individual's insulin sensitivity, their eating habits, and their diet. People with T1D often use 3-4 carbohydrate ratios per day (i.e., one ratio per main meal).

The basal insulin dose and carbohydrate ratios, collectively referred to as the MDI therapy parameters, are specific to each individual and are periodically adjusted to improve overall glycemic control. Advances in glucose monitoring systems have made it possible for people with T1D and health care professionals to view daily glucose levels and adjust the MDI therapy parameters.

However, this process is subjective, error-prone, and time-consuming. Moreover, in addition to glucose levels, one must consider insulin doses, type and amount of meals, and activity levels when adjusting the MDI therapy parameters.

SUMMARY

It is an object of one or more embodiments of the present technology to improve at least one of the limitations present in the prior art. One or more embodiments of the present technology may provide and/or broaden the scope of approaches to and/or methods of achieving the aims and objects of the present technology.

One or more embodiments of the present technology have been developed based on developers' appreciation that multiple daily injections (MDI) therapy is the most common treatment for type 1 diabetes (T1D). MDI therapy includes (i) basal insulin doses, often once daily, to keep glucose levels constant during fasting conditions and (ii) bolus insulin doses with meals to metabolize their carbohydrates. Optimal insulin dosing is critical to achieving satisfactory glycemia but is challenging due to inter- and intra-individual variability.

More specifically, developers have appreciated that different techniques could be developed for optimizing insulin doses for administration to a diabetic subject using previous-day glucose, insulin, and meal data.

Thus, one or more embodiments of the present technology are directed to a method of and a system for determining recommended therapy parameters for a diabetic subject.

In accordance with a broad aspect of the present technology, there is provided a method for determining recommended multiple daily injections (MDI) therapy values for administering to a given subject, the method is executed by a processor. the method comprises: receiving a consumed meal by the given subject, an insulin basal dose administered to the given subject, and an insulin bolus dose administered to the given subject, receiving an initial meal ratio parameter and an initial basal insulin dose used by the given subject. The method comprises determining, based on the consumed meal by the given subject, the insulin basal dose, the insulin bolus doses, and the initial meal ratio parameter, a predicted glucose concentration parameter, receiving an actual glucose concentration parameter, estimating, using the predicted glucose concentration parameter, the actual glucose concentration parameter, a set of optimal MDI therapy parameters, and determining, based on the set of optimal MDI therapy parameters, a set of recommended MDI therapy parameters, the set of recommended MDI therapy parameters includes an optimal meal ratio parameter, and an optimal basal insulin dose to be administered to the given subject.

In one or more embodiments of the method, said estimating, using the predicted glucose concentration parameter, the actual glucose concentration parameter, the set of optimal MDI therapy parameters comprises determining a confidence in the optimal MDI therapy parameters, and said determining, based on the set of optimal MDI therapy parameters, the set of recommended MDI therapy parameters, the set of recommended MDI therapy parameters comprising the optimal meal ratio parameter, and the optimal basal insulin dose to be administered to the given subject is further based on the confidence in the optimal MDI therapy parameters.

In one or more embodiments of the method, the method further comprises, prior to said determining the predicted glucose concentration parameter: determining, based on the consumed meal, a rate of meal glucose appearance determining, based on the insulin basal dose and an initial optimal basal insulin dose, a first rate of insulin appearance in response to the insulin basal dose, determining, based on the meal ratio parameter and the insulin bolus dose, a second rate of insulin appearance in response to the insulin bolus dose, said determining the glucose concentration parameter is further based on: the rate of meal glucose appearance, the first rate of insulin appurtenance, and the second rate of insulin appearance.

In one or more embodiments of the method, said estimating the set of optimal MDI therapy parameters comprises: initializing a set of model parameters, and determining, a set of model parameters estimates, the set of model parameters estimates includes the set of optimal MDI therapy parameters, the determining is based on: the set of model parameters, the predicted glucose concentration parameter, the actual glucose concentration parameter, and the consumed meal by the given subject, the insulin basal dose, the insulin bolus dose, and the initial meal ratio parameter.

In one or more embodiments of the method, said determining the predicted glucose concentration parameter is further based on: an insulin sensitivity, a time-to-peak (TTP) of insulin action, a carbohydrate sensitivity, and a TTP of carbohydrate absorption.

In one or more embodiments of the method, said estimating is performed using a gradient descent optimization, and a Monte-Carlo Markov Chain (MCMC) sampling.

In one or more embodiments of the method, the consumed meal comprises an estimated weight of carbohydrates in the meal.

In one or more embodiments of the method, the optimal meal ratio is a carbohydrate ratio for pre-meal glucose values.

In one or more embodiments of the method, the glucose concentration parameter is an interstitial glucose concentration.

In one or more embodiments of the method, said estimating comprises using a maximum a posteriori (MAP) estimate.

In one or more embodiments of the method, the MAP estimate is obtained using: $p^* = \arg\max_p \mathcal{P}(p|Y_{1:N}, U_{1:N})$ $\Leftrightarrow P^* = \arg\max_p \mathcal{P}(Y_{1:N}|U_{1:N}, p)\mathcal{P}(p)$, where $Y_{1:N}$ is the actual glucose concentration parameter $U_{1:N}$ is a set of inputs includes the consumed meal by the given subject, the insulin basal dose, the insulin bolus dose, and the initial meal ratio parameter, p is the set of model parameters.

In one or more embodiments of the method, the method further comprises, prior to said determining the set of recommended MDI therapy parameters: determining a coefficient of variation (CV) of the set of MDI therapy parameters, determining local mean absolute error (MAE) of the difference between the observed glucose levels and the predicted glucose resulting from the fit, and determining a learning rate coefficient based on the CV and the MAE, said determining the set of recommended MDI therapy parameters is further based on a learning rate coefficient.

In one or more embodiments of the method, the method further comprises, prior to said determining the set of recommended MDI therapy parameters: determining a saturation function, and said determining the set of recommended MDI therapy parameters is obtained using:

$$X_{d+1} = X_d + \phi(\eta(\mathbb{E}[\widehat{X_d}] - X_d))$$

where $X_{d+1}$ is the recommended set of MDI therapy parameters, $X_d$ is an initial set of therapy parameters, $\mathbb{E}[\widehat{X_d}]$ is the estimated optimal therapy parameter, $\eta$ is the learning rate and $\phi$ is the saturation function.

In accordance with a broad aspect of the present technology, there is provided a method for determining optimal multiple daily injections (MDI) therapy values for administering to a given subject, the method is executed by a processor. the method comprises: Initializing with an initial meal ratio parameter and an initial basal insulin dose previously used by the given subject, receiving actual glucose concentrations, consumed meals by the given subject, insulin basal doses administered to the given subject, and insulin bolus doses administered to the given subject, estimating, using the predicted glucose concentration, the optimal MDI therapy parameters, and the confidence in the optimal MDI therapy parameters, determining, based on the set of optimal MDI therapy parameters, a set of recommended MDI therapy parameters, the set of MDI therapy parameters includes meal ratios parameter, and a basal insulin dose.

In one or more embodiments of the method, the method further comprises, prior to the determining the predicted glucose concentration parameter: determining, based on the consumed meal, a rate of meal glucose appearance determining, based on the insulin basal dose and the optimal basal insulin dose, a first rate of insulin appearance in response to the insulin basal dose, determining, based the insulin bolus dose and on the optimal meal ratio parameter, a second rate of insulin appearance in response to the insulin bolus dose, the predicted glucose concentration parameter is further based on: the rate of meal glucose appearance, the first rate of insulin appurtenance, and the second rate of insulin appearance.

In one or more embodiments of the method, the estimating the set of current MDI therapy parameters comprises: initializing a set of subject model parameters, and initializing a set of therapy parameters meal ratios parameter, and a basal insulin dose, and determining, a set of optimal model parameters estimates, and optimal therapy parameters by comparing the actual glucose concentrations to the model predictions of glucose concentrations, knowing consumed meal by the given subject, the insulin basal doses, the insulin bolus doses.

In one or more embodiments of the method, the determining the set of recommended MDI therapy parameters comprises: initializing a set of therapy parameters, estimating a set of optimal therapy parameters, and estimating a learning rate.

In one or more embodiments of the method, the determining the predicted glucose concentration parameter is further based on: an insulin sensitivity, a time-to-peak (TTP) of insulin action, a carbohydrate sensitivity, and a TTP of carbohydrate absorption.

In one or more embodiments of the method, the estimating comprises using a maximum a posteriori (MAP) estimate.

In one or more embodiments of the method, the solving of the maximum a posteriori (MAP) estimate is performed using a gradient descent optimization, and a Monte-Carlo Markov Chain (MCMC) sampling.

In one or more embodiments of the method, the consumed meal comprises an estimated amount of carbohydrates in the meal.

In one or more embodiments of the method, the glucose concentration parameter is an interstitial glucose concentration.

In one or more embodiments of the method, the MAP estimate is obtained using: $p^* = \arg\max_p \mathcal{P}(Y_{1:N}|U_{1:N}, p)\mathcal{P}(p)$, where $Y_{1:N}$ is the actual glucose concentration parameter $U_{1:N}$ is a set of inputs includes the consumed meal by the given subject, the insulin basal dose, the insulin bolus dose, p is the set of model parameters includes of model parameters and therapy parameters.

In one or more embodiments of the method, the method comprises prior to said determining the set of recommended MDI therapy parameters: determining a coefficient of variation of the set of MDI therapy parameters, determining local mean absolute error (MAE) of the difference between the observed glucose levels and the predicted glucose resulting from the fit, and determining a learning rate coefficient based on the CV and the MAE, and determining a saturation function, and the determining the set of optimal MDI therapy parameters is further based on: $X_{d+1}=X_d+\phi(\eta(\mathbb{E}[\widehat{X_d}]-X_d))$, where $X_{d+1}$ are recommended set of therapy parameters, $X_d$ are initial set of therapy parameters, $\mathbb{E}[\widehat{X_d}]$ are the estimated optimal therapy parameter, $\eta$ is a learning rate and $\phi$ is a saturation function.

In accordance with a broad aspect of the present technology, there is provided a system for determining optimal multiple daily injections (MDI) therapy values for administering to a given subject. the system comprises: a processor, a non-transitory computer-readable storage medium operatively connected to the processor, the computer-readable storage medium includes instructions. The processor, upon executing the instructions, is configured for: receiving a consumed meal by the given subject, an insulin basal dose administered to the given subject, and an insulin bolus dose administered to the given subject, receiving an initial meal ratio parameter and an initial basal insulin dose used by the given subject, determining, based on the consumed meals by the given subject, the insulin basal dose, the insulin bolus doses, and the initial meal ratio parameter, a predicted glucose concentration parameter, receiving an actual glucose concentration parameter, estimating, using the predicted glucose concentration parameter, the actual glucose concentration parameter, a set of optimal MDI therapy parameters, and determining, based on the set of optimal MDI therapy parameters, a set of recommended MDI therapy parameters, the set of recommended MDI therapy parameters includes an optimal meal ratio parameter, and an optimal basal insulin dose to be administered to the given subject.

In one or more embodiments of the system, the processor is further configured for, prior to the determining the predicted glucose concentration parameter: determining, based on the consumed meal, a rate of meal glucose appearance, determining, based on the insulin basal dose and an initial optimal basal insulin dose, a first rate of insulin appearance in response to the insulin basal dose, determining, based on the meal ratio parameter and the insulin bolus dose, a second rate of insulin appearance in response to the insulin bolus dose, the determining the glucose concentration parameter is further based on: the rate of meal glucose appearance, the first rate of insulin appurtenance, and the second rate of insulin appearance.

In one or more embodiments of the system, said estimating the set of optimal MDI therapy parameters comprises: initializing a set of model parameters, and determining, a set of model parameters estimates, the set of model parameters estimates includes the set of optimal MDI therapy parameters, the determining is based on: the set of model parameters, the predicted glucose concentration parameter, the actual glucose concentration parameter, and the consumed meal by the given subject, the insulin basal dose, the insulin bolus dose, and the initial meal ratio parameter.

In one or more embodiments of the system, said determining the predicted glucose concentration parameter is further based on: an insulin sensitivity, a time-to-peak (TTP) of insulin action, a carbohydrate sensitivity, and a TTP of carbohydrate absorption.

In one or more embodiments of the system, said estimating is performed using a gradient descent optimization, and a Monte-Carlo Markov Chain (MCMC) sampling.

In one or more embodiments of the system, the consumed meal comprises an estimated weight of carbohydrates in the meal.

In one or more embodiments of the system, the optimal meal ratio is a carbohydrate ratio for pre-meal glucose values.

In one or more embodiments of the system, the glucose concentration parameter is an interstitial glucose concentration.

In one or more embodiments of the system, said estimating comprises using a maximum a posteriori (MAP) estimate.

In one or more embodiments of the system, the MAP estimate is obtained using: $p^*=\arg\max_p \mathcal{P}(p|Y_{1:N},U_{1:N}) \Leftrightarrow p^*=\arg\max_p \mathcal{P}(Y_{1:N}|U_{1:N},p)\mathcal{P}(p)$, where $Y_{1:N}$ is the actual glucose concentration parameter $U_{1:N}$ is a set of inputs includes the consumed meal by the given subject, the insulin basal dose, the insulin bolus dose, and the initial meal ratio parameter, p is the set of model parameters.

In one or more embodiments of the system, the processor is further configured for, prior to said determining the set of recommended MDI therapy parameters: determining a coefficient of variation (CV) of the set of MDI therapy parameters, determining local mean absolute error (MAE) of the difference between the observed glucose levels and the predicted glucose resulting from the fit, and determining a learning rate coefficient based on the CV and the MAE, said determining the set of recommended MDI therapy parameters is further based on a learning rate coefficient.

In one or more embodiments of the system, the processor is further configured for, prior to said determining the set of recommended MDI therapy parameters: determining a saturation function, and said determining the set of recommended MDI therapy parameters is obtained using:

$$X_{d+1}=X_d+\phi(\eta(\mathbb{E}[\widehat{X_d}]-X_d))$$

where $X_{d+1}$ is the recommended set of MDI therapy parameters, $X_d$ is an initial set of therapy parameters, $\mathbb{E}[\widehat{X_d}]$ is the estimated optimal therapy parameter, $\eta$ is the learning rate and $\phi$ is the saturation function.

In one or more embodiments of the system, said estimating, using the predicted glucose concentration parameter, the actual glucose concentration parameter, the set of optimal MDI therapy parameters comprises determining a confidence in the optimal MDI therapy parameters, and said determining, based on the set of optimal MDI therapy parameters, the set of recommended MDI therapy parameters, the set of recommended MDI therapy parameters comprising the optimal meal ratio parameter, and the optimal basal insulin dose to be administered to the given subject is further based on the confidence in the optimal MDI therapy parameters.

Definitions

In the context of the present specification, a "server" is a computer program that is running on appropriate hardware and is capable of receiving requests (e.g., from electronic devices) over a network (e.g., a communication network), and carrying out those requests, or causing those requests to be carried out. The hardware may be one physical computer or one physical computer system, but neither is required to be the case with respect to the present technology. In the present context, the use of the expression a "server" is not intended to mean that every task (e.g., received instructions or requests) or any particular task will have been received, carried out, or caused to be carried out, by the same server (i.e., the same software and/or hardware); it is intended to mean that any number of software elements or hardware devices may be involved in receiving/sending, carrying out or causing to be carried out any task or request, or the consequences of any task or request; and all of this software and hardware may be one server or multiple servers, both of which are included within the expressions "at least one server" and "a server".

In the context of the present specification, "electronic device" is any computing apparatus or computer hardware that is capable of running software appropriate to the relevant task at hand. Thus, some (non-limiting) examples of electronic devices include general purpose personal computers (desktops, laptops, netbooks, etc.), mobile computing devices, smartphones, and tablets, and network equipment such as routers, switches, and gateways. It should be noted that an electronic device in the present context is not precluded from acting as a server to other electronic devices. The use of the expression "an electronic device" does not preclude multiple electronic devices being used in receiving/sending, carrying out or causing to be carried out any task or request, or the consequences of any task or request, or steps of any method described herein. In the context of the present specification, a "client device" refers to any of a range of end-user client electronic devices, associated with a user, such as personal computers, tablets, smartphones, and the like.

In the context of the present specification, the expression "computer readable storage medium" (also referred to as "storage medium" and "storage") is intended to include non-transitory media of any nature and kind whatsoever, including without limitation RAM, ROM, disks (CD-ROMs, DVDs, floppy disks, hard drivers, etc.), USB keys, solid state-drives, tape drives, etc. A plurality of components may be combined to form the computer information storage media, including two or more media components of a same type and/or two or more media components of different types.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, unless expressly provided otherwise, an "indication" of an information element may be the information element itself or a pointer, reference, link, or other indirect mechanism enabling the recipient of the indication to locate a network, memory, database, or other computer-readable medium location from which the information element may be retrieved. For example, an indication of a document may include the document itself (i.e. its contents), or it may be a unique document descriptor identifying a file with respect to a particular file system, or some other means of directing the recipient of the indication to a network location, memory address, database table, or other location where the file may be accessed. As one skilled in the art will appreciate, the degree of precision required in such an indication depends on the extent of any prior understanding about the interpretation to be given to information being exchanged as between the sender and the recipient of the indication. For example, if it will be appreciated that prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, the expression "communication network" is intended to include a telecommunications network such as a computer network, the Internet, a telephone network, a Telex network, a TCP/IP data network (e.g., a WAN network, a LAN network, etc.), and the like. The term "communication network" includes a wired network or direct-wired connection, and wireless media such as acoustic, radio frequency (RF), infrared and other wireless media, as well as combinations of any of the above.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it will be appreciated that, the use of the terms "server" and "third server" is not intended to imply any particular order, type, chronology, hierarchy or ranking (for example) of/between the server, nor is their use (by itself) intended imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Implementations of the present technology each have at least one of the above-mentioned objects and/or aspects, but do not necessarily have all of them. It will be appreciated that some aspects of the present technology that have resulted from attempting to attain the above-mentioned object may not satisfy this object and/or may satisfy other objects not specifically recited herein.

Additional and/or alternative features, aspects and advantages of implementations of one or more embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
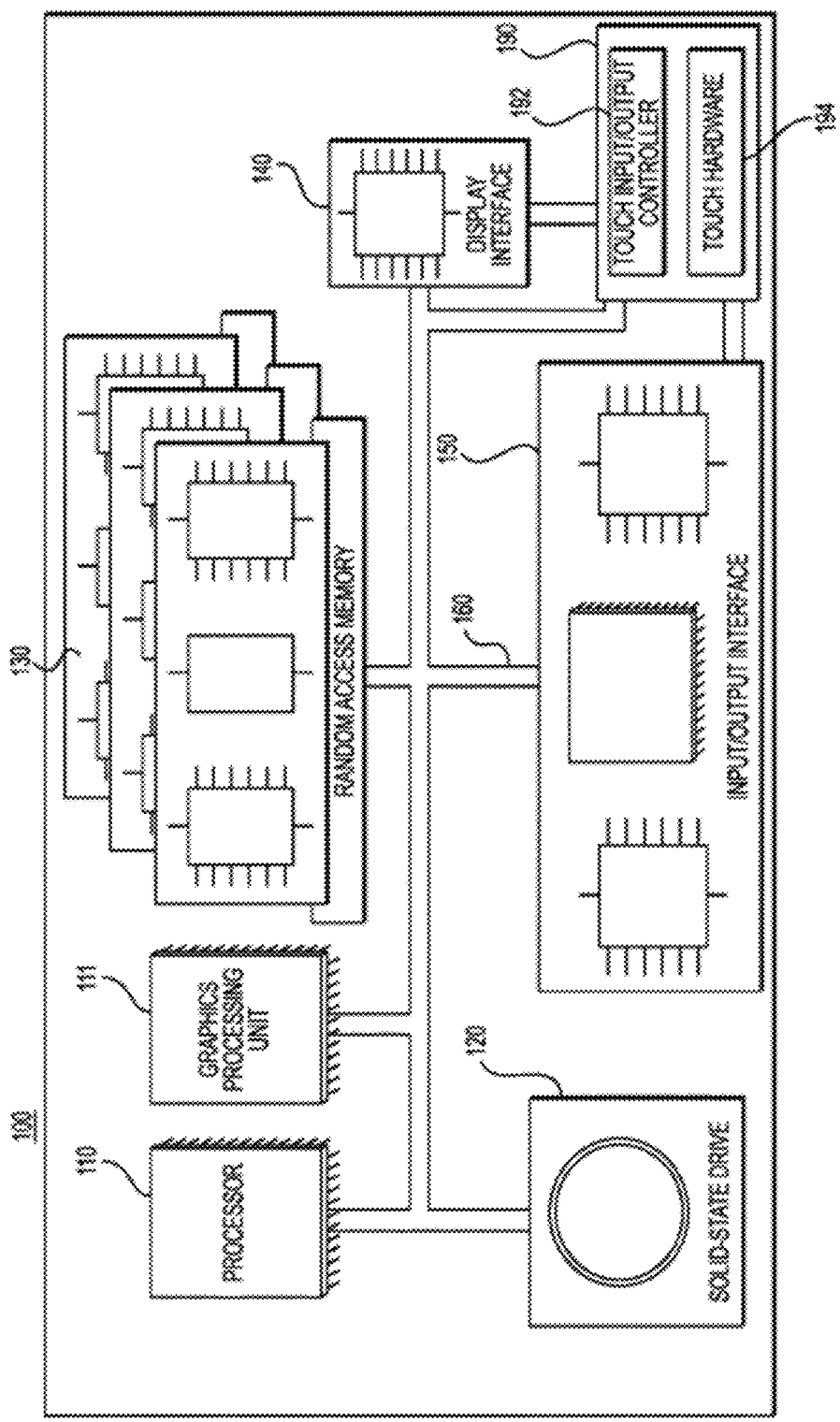
FIG. 1 depicts a schematic diagram of an electronic device in accordance with one or more non-limiting embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology.

Furthermore, as an aid to understanding, the following description may describe relatively simplified implementations of the present technology. As a person skilled in the art will appreciate, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by the skilled addressee that any block diagram herein represents conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some non-limiting embodiments of the present technology, the processor may be a general purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

Electronic Device

Now referring to FIG. 1, there is shown an electronic device 100 suitable for use with one or more implementations of the present technology, the electronic device 100 comprises various hardware components including one or more single or multi-core processors collectively represented by processor 110, a graphics processing unit (GPU) 111, a solid-state drive 120, a random access memory 130, a display interface 140, and an input/output interface 150.

Communication between the various components of the electronic device 100 may be enabled by one or more internal and/or external buses 160 (e.g. a PCI bus, universal serial bus, IEEE 1394 "Firewire" bus, SCSI bus, Serial-ATA bus, etc.), to which the various hardware components are electronically coupled.

The input/output interface 150 may be coupled to a touchscreen 190 and/or to the one or more internal and/or external buses 160. The touchscreen 190 may be part of the display. In one or more embodiments, the touchscreen 190 is the display. The touchscreen 190 may equally be referred to as a screen 190. In the embodiment illustrated in FIG. 1, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In one or more embodiments, the input/output interface 150 may be connected to a keyboard (not shown), a mouse (not shown) or a trackpad (not shown) enabling the user to interact with the electronic device 100 in addition or in replacement of the touchscreen 190.

According to one or more implementations of the present technology, the solid-state drive 120 stores program instructions suitable for being loaded into the random-access memory 130 and executed by the processor 110 and/or the GPU 111. For example, the program instructions may be part of a library or an application.

It will be appreciated that the electronic device 100 may be implemented as a server, a desktop computer, a laptop computer, a tablet, a smartphone, a personal digital assistant or any device that may be configured to implement the present technology, as it may be appreciated by a person skilled in the art.

System

Figure 2:
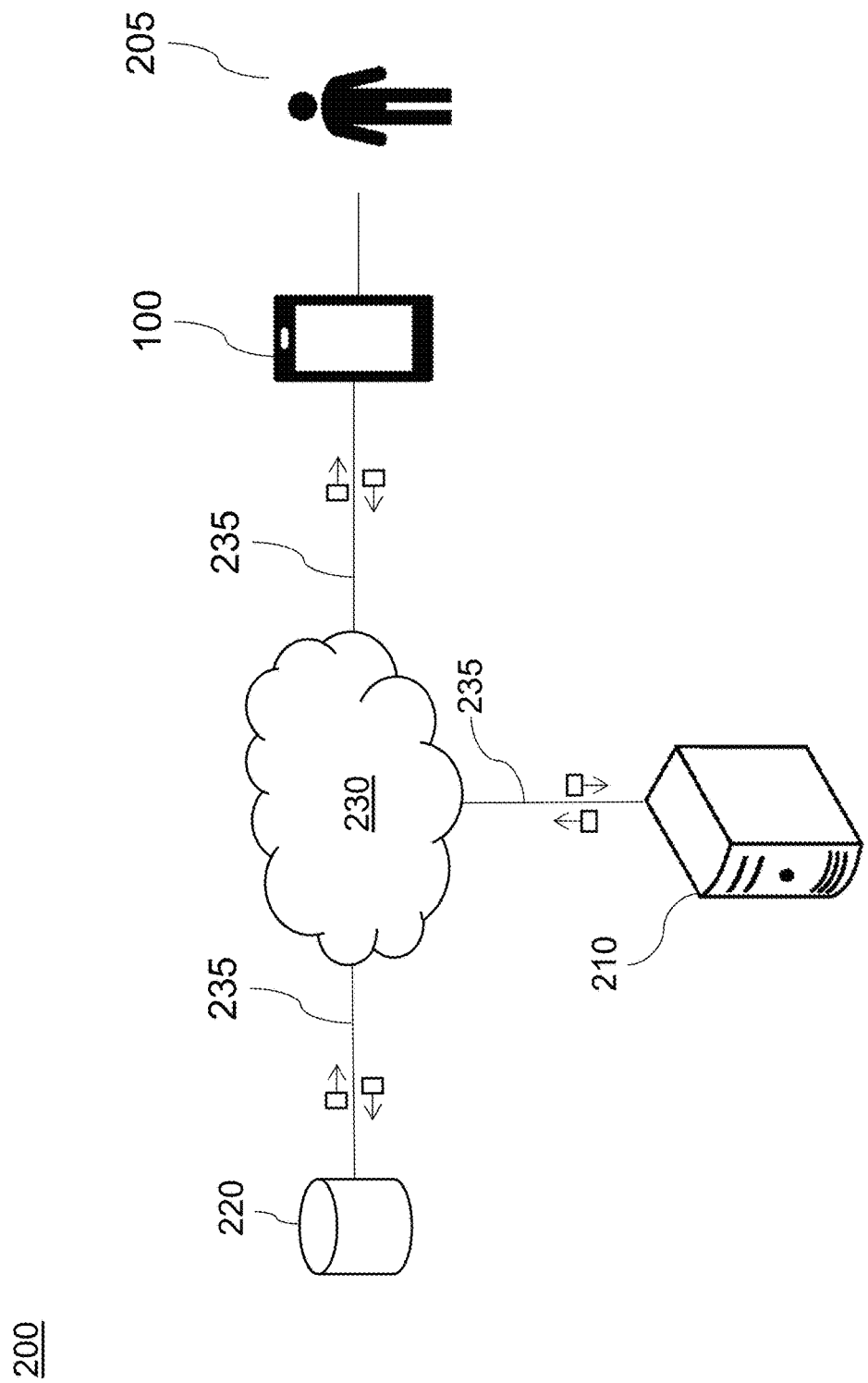
FIG. 2 depicts a schematic diagram of a system in accordance with one or more non-limiting embodiments of the present technology.

Now referring to FIG. 2, there is shown a schematic diagram of a system 200, the system 200 being suitable for implementing one or more non-limiting embodiments of the present technology. It will be appreciated that the system 200 as shown is merely an illustrative implementation of the present technology. Thus, the description thereof that follows is intended to be only a description of illustrative examples of the present technology. In some cases, what are believed to be helpful examples of modifications to the system 200 may also be set forth below. This is done merely as an aid to understanding, and, again, not to define the scope or set forth the bounds of the present technology. These modifications are not an exhaustive list, and, as a person skilled in the art will understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art will appreciate, this is likely not the case. In addition, it will be appreciated that the system 200 may provide in certain instances simple implementations of one or more embodiments of the present technology, and that where such is the case they have been presented in this manner as an aid to understanding.

The system 200 comprises inter alia the electronic device 100 associated with a diabetic user 205, a server 210, and a database 220 communicatively coupled over a communications network 230 via respective communication links 235.

The electronic device 100 is associated with the diabetic user 205 or diabetic subject 205. As a non-limiting example, the electronic device 100 may be implemented as a smartphone of the diabetic user 205. The diabetic user 205 may input information relating to his health and diabetes into the electronic device 100, which stores the information into the database 220. In one embodiment, the electronic device 100 may be part of an artificial pancreas system (e.g. in a component of the artificial pancreas system). In an alternative embodiment, the electronic device 100 may be a desktop computer of the diabetic user 205.

The diabetic user 205 may input, for example via the touchscreen 190, consumed meals, received insulin basal doses, and received insulin bolus doses, which may be stored in the solid-state drive 120, the random-access memory 130, or transmitted for storage in the database 220.

In one or more embodiments, the diabetic user 205 is associated with an artificial pancreas system (not shown) which includes one or more of: a continuous glucose monitoring system (CGM), an insulin infusion pump, and a control procedure.

The CGM system provides a steady stream of information that reflects the user's 205 blood glucose levels. The CGM comprises a sensor placed subcutaneously under the patient's skin (not depicted) which measures the glucose in the fluid around the cells (interstitial fluid) which is associated with blood glucose levels. The CGM system may have a user interface such as a screen or touchscreen (not depicted) and/or may transmit the glucose related information to the electronic device 100 of the diabetic user 205 or another electronic device (not depicted) via a communication link (not numbered) over a communication network (not depicted). In one or more embodiments, the glucose monitoring system transmits information reflecting the user's 205 blood glucose levels for storage in the database 220.

In one or more alternative embodiments, the diabetic user 205 uses a blood glucose meter for determining approximate concentrations of blood glucose, which may be stored in the electronic device 100, in another electronic device (not shown) or in the database 220 for example.

Server

The server 210 is configured to: (i) receive data related to meals consumed meal by the diabetic user 205, insulin basal doses and insulin bolus doses administered to the diabetic user 205; (ii) predict, based on the consumed meals, the insulin basal and bolus doses, blood glucose concentration; (iii) estimate, using the predicted glucose concentration, measured glucose concentration, a set of current or optimal multiple daily injections (MDI) parameters for a given time period; and (iv) determine, based on the set of optimal MDI therapy parameters, a set of optimal MDI therapy parameters to be used for administering to the diabetic user 205.

How the server 210 is configured to do so will be explained in more detail herein below.

It will be appreciated that the server 210 can be implemented as a conventional computer server and may comprise at least some of the features of the electronic device 100 shown in FIG. 1. In a non-limiting example of one or more embodiments of the present technology, the server 210 is implemented as a Dell™ PowerEdge™ Server running the Microsoft™ Windows Server™ operating system. Needless to say that the server 210 may be implemented in any other suitable hardware and/or software and/or firmware or a combination thereof. In the disclosed non-limiting embodiment of present technology, the server 210 is a single server. In one or more alternative non-limiting embodiments of the present technology, the functionality of the server 210 may be distributed and may be implemented via multiple servers (not shown).

It will be appreciated that the implementation of the server 210 is well known to the person skilled in the art. However, the server 210 comprises a communication interface (not shown) configured to communicate with various entities (such as the database 220, for example and other devices potentially coupled to the communication network 230) via the network. The server 210 further comprises at least one computer processor (e.g., the processor 110 of the electronic device 100) operationally connected with the communication interface and structured and configured to execute various processes to be described herein.

Database

A database 220 is communicatively coupled to the server 210 via the communications network 230 but, in one or more alternative implementations, the database 220 may be communicatively coupled to the server 210 without departing from the teachings of the present technology. Although the database 220 is illustrated schematically herein as a single entity, it will be appreciated that the database 220 may be configured in a distributed manner, for example, the database 220 may have different components, each component being configured for a particular kind of retrieval therefrom or storage therein.

The database 220 may be a structured collection of data, irrespective of its particular structure or the computer hardware on which data is stored, implemented or otherwise rendered available for use. The database 220 may reside on the same hardware as a process that stores or makes use of the information stored in the database 220 or it may reside on separate hardware, such as on the server 210. The database 220 may receive data from the server 210 for storage thereof and may provide stored data to the server 210 for use thereof.

In one or more embodiments of the present technology, the database 220 is configured to store, for one or more subjects such as the diabetic user 205: (i) data related to consumed meals, and administered insulin basal doses and insulin bolus doses; (ii) predicted glucose concentrations and measured glucose concentrations; and (iii) a set of MDI therapy parameters and a set of optimal MDI therapy parameters, as well as data used for determining predicted glucose concentrations and the set of optimal MDI therapy parameters.

Communication Network

In one or more embodiments of the present technology, the communications network 230 is the Internet. In one or more alternative non-limiting embodiments, the communication network 230 may be implemented as any suitable local area network (LAN), wide area network (WAN), a private communication network or the like. It will be appreciated that implementations for the communication network 230 are for illustration purposes only. How a communication link 235 (not separately numbered) between the server 210, the database 220, and/or another electronic device (not shown) and the communications network 230 is implemented will depend inter alia on how each electronic device is implemented.

Glucose Concentration Prediction Procedure

Figure 3:
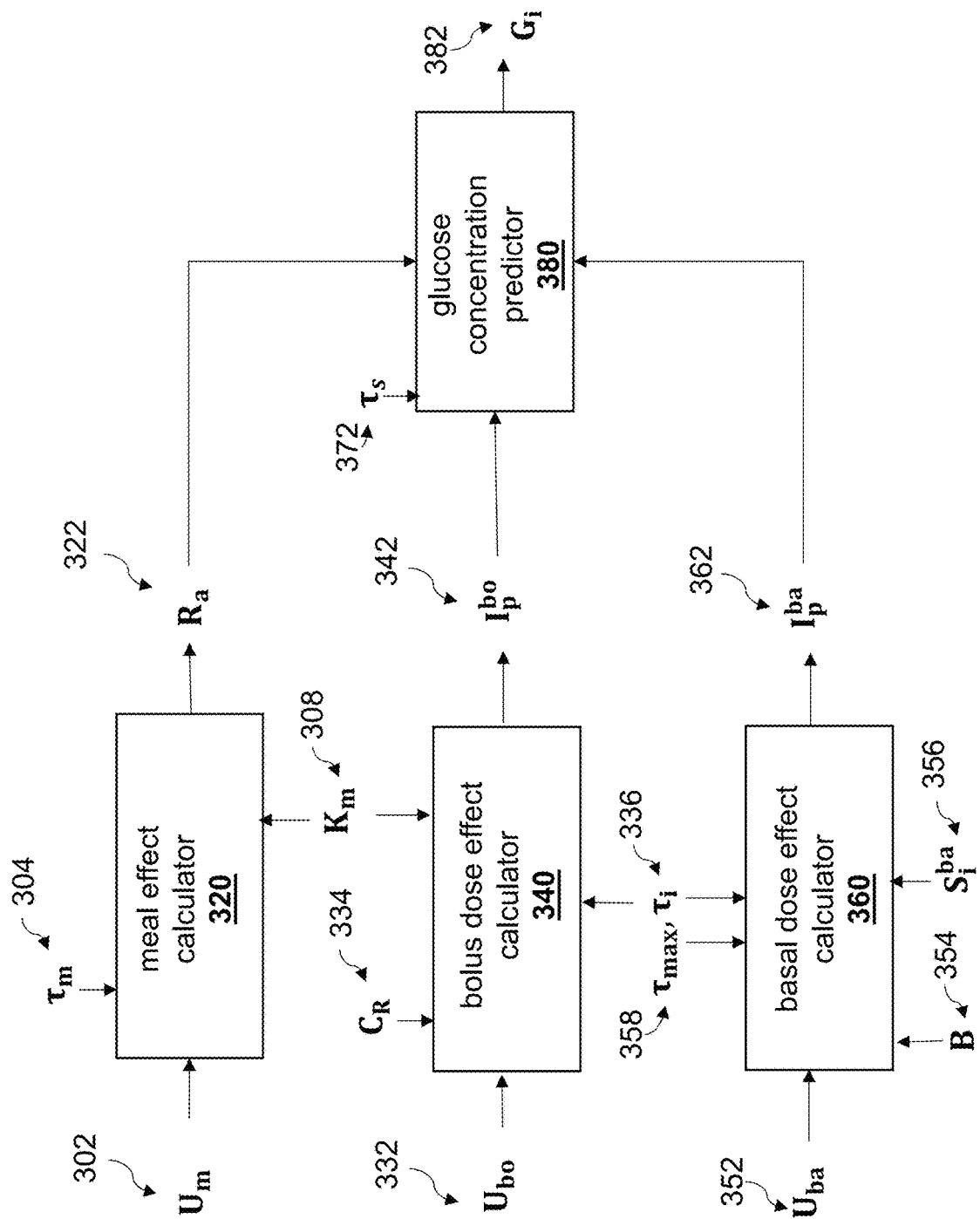
FIG. 3 depicts a schematic diagram of a glucose concentration prediction procedure in accordance with one or more non-limiting embodiments of the present technology.

With reference to FIG. 3 there is shown a schematic diagram of a glucose concentration prediction procedure 300 in accordance with one or more non-limiting embodiments of the present technology.

The glucose concentration prediction procedure 300 is executed by the server 210. It will be appreciated that the glucose concentration prediction procedure 300 may be executed by another electronic device comprising a processor such as the processor 110 or the GPU 111. In one or more alternative embodiments, the glucose concentration prediction procedure 300 is executed by the electronic device 100.

The glucose concentration prediction procedure 300 is performed via a meal effect calculator 320, a bolus dose effect calculator 340, a basal dose effect calculator 360 and a glucose concentration predictor 380.

Glucoregulatory Model Definitions

The mathematical variables used to describe model inputs, outputs and parameters include:

$U_m$ Amount of carbohydrates in consumed meal 302
$G_m$ Sensor glucose
B Optimal basal insulin dose 354
$C_R$ Optimal carbohydrate ratio 334
$S_i^{ba}$ Basal insulin sensitivity 356
$\tau_i$ Time-to-peak of insulin action 336
$K_m$ Carbohydrate sensitivity 308
$\tau_m$ Time-to-peak of carbohydrate absorption 304
$\tau_{max}$ Duration effect of insulin basal dose 358
$\tau_s$ Transfer-rate constant between plasma and interstitial glucose 372

The glucose concentration prediction procedure 300 is configured to: (i) receive an indication of a consumed meal 302, an insulin bolus dose 332, and an insulin basal dose 362 administered to the diabetic user 205; and (ii) determine a predicted glucose concentration parameter indicative of a blood glucose concentration in response to the diabetic user 205 having consumed the consumed meal 302, having been administered the insulin bolus dose 322, and having been administered the insulin basal dose 362. The predicted glucose concentration parameter may be a predicted plasma blood glucose concentration or a predicted interstitial glucose concentration.

Meal Effect Calculator

The meal effect calculator 320 is configured to: (i) receive an indication of a consumed meal 302; (ii) receive a carbohydrate sensitivity 308, and a time-to-peak (TTP) of carbohydrate absorption 304; (iii) determine, based on the consumed meal 302, the carbohydrate sensitivity 308, and the TTP of carbohydrate absorption 304, a rate of meal glucose appearance 322 in the blood after the consumed meal 302.

The rate of meal glucose appearance 332 in the blood represented by $R_a(t)$ (mmol/L/min) after the consumed meal 302 represented by $U_m$ is described by the two-compartment model expressed as equation (1):

$$R_a(t) = K_m \cdot \frac{U_m}{\tau_m^2} \cdot t \cdot e^{-\frac{t}{\tau_m}} \qquad (1)$$

where $K_n$, is the carbohydrate sensitivity 308, $U_m$ is an amount of carbohydrates in a consumed meal, and $\tau_m$ is a time-to-peak (TTP) of carbohydrate absorption 304 and t is time in minutes.

The meal effect calculator 320 receives as an input an indication of a consumed meal 302. In one or more embodiments, the consumed meal 302 is expressed as an amount of carbohydrates in the consumed meal 302. The consumed meal 302 is modelized as a delta Dirac function in the glucoregulatory system.

As a non-limiting example, the consumed meal 302 may be received from the database 220. As another non-limiting example, the indication of consumed meal 302 may be received from the electronic device 100 after the diabetic user 205 having input the consumed meal 302 via the touchscreen 190.

The meal effect calculator 320 receives the carbohydrate sensitivity 308. The carbohydrate sensitivity 308 is indicative of the diabetic user's 205 glucoregulatory system sensitivity to consumed carbohydrates. The carbohydrate sensitivity is a coefficient that converts carbohydrate amount consumed in a meal in grams to glucose concentration in mmol/L. The carbohydrate sensitivity 308 comprises or is based on the carbohydrates bioavailability and the volume of distribution of glucose.

The meal effect calculator 320 receives the time-to-peak (TTP) of carbohydrate absorption 304. In one or more embodiments, the TTP of carbohydrate absorption 304 is estimated for the meal, i.e. based on the consumed meal 302. As a non-limiting example, in one or more embodiments, the TTP of carbohydrate absorption 304 may be set as 10 min.

The meal effect calculator 320 integrates the rate of glucose appearance from meals and disappearance due to insulin over time.

The meal effect calculator 320 determines the rate of meal glucose appearance 322 into the blood circulation based on: the consumed meal 302, the carbohydrate sensitivity 308, and the TTP of carbohydrate absorption 304.

In one or more embodiments, the meal effect calculator 320 determines the rate of meal glucose appearance 322 by: multiplying the consumed meal 302 and the carbohydrate sensitivity 308, and dividing the result of the multiplication by the squared sum of the TTP of carbohydrate absorption 304 and one.

Mathematically, the Laplace transform of the rate of meal glucose appearance 322 in the blood after the consumed meal 302 is expressed as equation (2):

$$R_a(t) = \frac{K_m U_m}{(\tau_m s + 1)^2} \tag{2}$$

where $R_a(t)$ is the rate of meal glucose appearance 322 (mmol/L/min) in the blood, $U_m$ is an amount of carbohydrates in a consumed meal 302, $\tau_m$ is the duration effect of insulin basal dose (min), $K_m$ is the carbohydrate sensitivity 308, and $\tau_m$ is the TTP of carbohydrate absorption 304. It will be appreciated that equation (2) is the Laplace transform of equation (1).

The meal effect calculator 320 outputs the rate of meal glucose appearance 322 in the blood after the ingested meal 302.

Bolus Dose Effect Calculator

The bolus dose effect calculator 340 is configured to: (i) receive an insulin bolus dose 332; (ii) receive an initial estimated carbohydrate ratio 334; (iii) receive the carbohydrate sensitivity 308, a time-to-peak of insulin action 336; and (iv) determine, based on the insulin bolus dose 332, the initial estimated carbohydrate ratio 334, the carbohydrate sensitivity 308, the TTP of insulin action 336, a first rate of insulin appearance 342 in the blood after an insulin bolus dose 332.

The first rate of insulin appearance 342 in the blood $I_p^{bo}$ (t(U/min) after an insulin bolus dose 332 represented by $U_{bo}$ is described by the two-compartment model expressed as equation (3):

$$I_p^{bo}(t) = \frac{U_{bo}}{\tau_i^2} \cdot t \cdot e^{-\frac{t}{\tau_i}} \tag{3}$$

Where $\tau_i$ is a time-to-peak of insulin action.

At mealtimes, people with T1D deliver an insulin bolus dose proportional to the carbohydrates in the meal. The changes in post-meal plasma glucose levels are determined by the combined action of the insulin bolus and meal glucose expressed as equation (5):

$$\frac{dG_p(t)}{dt} = -S_i^{bo} \cdot I_p^{bo}(t) + R_a(t) \tag{4}$$

where $S_i^{bo}$ (mmol/L/U) is the bolus insulin sensitivity. The solution of (4) is:

$$G_p(t) = \tag{5}$$
$$G_p(0) - S_i^{bo}\left(1 - e^{-\frac{t}{\tau_i}} - \frac{t}{\tau_i}e^{-\frac{t}{\tau_i}}\right)U_{bo} + K_m\left(1 - e^{\frac{t}{\tau_m}} - \frac{t}{\tau_m}e^{-\frac{t}{\tau_m}}\right)U_m$$

The optimal carbohydrate ratio 334 (i.e., $C_R$) is the ratio that leads to glucose levels eventually returning to their pre-meal glucose values. That is, $\lim_{t \to \infty}(t)=G(0)$, after a bolus $$U_{bo} = \frac{U_{meal}}{C_R}$$

is taken. In equation (5), the unique carbohydrate ratio that satisfies this condition is expressed as equation (6):

$$C_R = \frac{S_i^{bo}}{K_m} \tag{6}$$

The bolus dose effect calculator 340 receives the insulin bolus dose 332. In one or more embodiments, the insulin bolus dose 332 is expressed in (U) units. The insulin bolus dose 332 is modelized as a delta Dirac function in the glucoregulatory system of the diabetic user 205.

The bolus dose effect calculator 340 receives an initial estimated carbohydrate ratio 334. The initial estimated carbohydrate ratio 334 is the ratio that leads to glucose levels eventually returning to their pre-meal glucose values. In one or more embodiments, the initial estimated carbohydrate ratio is expressed in grams per unit (g/U).

The bolus dose effect calculator 340 receives the bolus insulin sensitivity which is related to the carbohydrate ratio and the carbohydrate sensitivity 308 via equation (6).

The bolus dose effect calculator 340 receives the TTP of insulin action 336.

The bolus dose effect calculator 340 determines, based on the insulin bolus dose 332, the initial estimated carbohydrate ratio 334, the carbohydrate sensitivity 308, the time-to-peak of insulin action 336, a first rate of insulin appearance 342 in the blood after the insulin bolus dose 332.

In one or more embodiments, to obtain the first rate of insulin appearance 342, the bolus dose effect calculator 340 multiplies the insulin bolus dose 332 by the initial estimated carbohydrate ratio 334, and the carbohydrate sensitivity 308. The bolus dose effect calculator 340 then divides the result by the squared sum of the TTP of carbohydrate absorption 304 plus one.

In one or more embodiments, the bolus dose effect calculator 340 determines the Laplace transform of the first rate of insulin appearance 342 using equation (7):

$$I_p^{bo} = \frac{C_R \cdot K_m \cdot U_{bo}}{(\tau_i s + 1)^2} \quad (7)$$

where $I_p^{bo}$ (t) is the first rate of insulin appearance 342 in the blood (U/min) after an insulin bolus dose 332 represented by $U_{bo}$ (U), $C_R$ is the optimal carbohydrate ratio 334 (g/U), $K_m$ is the carbohydrate sensitivity 308 (mmol/L/g), and $\tau_i$ is the time-to-peak of insulin action 336. It will be appreciated that equation (7) is the Laplace transform of equation (3).

The bolus dose effect calculator 340 outputs the first rate of insulin appearance 342 in the blood after the insulin bolus dose 332.

Basal Insulin Dose Effect Calculator

Long-acting insulin doses result in a slow, sustained release of insulin into the blood circulation. Models describing the pharmacokinetics of long-acting insulins exist in the literature. However, rather than modelling the pharmacokinetics of long-acting insulin, the effect of the quantity $U_{ba}$–B on glucose changes can be modelled, where $U_{ba}$ is the injected basal insulin dose 352, and B is the unknown optimal basal dose 354 that would maintain glucose level constant during fasting conditions. Delivering insulin more than the optimal dose would lead to continuously decreasing glucose levels, while delivering a dose below the optimal dose would lead to continuously increasing glucose levels. This motivates the following simple model for the basal pathway:

$$\frac{dG_p(t)}{dt} = -S_i^{ba}(I_p^{ba}(t) - I_{p0}(t)) \quad (8)$$

where $I_p^{ba}$(t) (U/min) is the second rate of insulin appearance 362 into the blood circulation due to basal dose 352 represented by $U_{ba}$, $I_{p0}$(t)(U/min) is the rate of insulin appearance into the blood that is needed to keep glucose levels steady and which results from the optimal basal dose 354 represented by B. The second rate of insulin appearance 362 represented by ($I_p^{ba}$(t)) into the blood circulation due to a long-acting insulin dose 352 represented by $U_{ba}$ can be described by the following trapezoid equation:

$$I_p^{ba}(t) = \begin{cases} \left(1 - \left(\frac{t}{\tau_i} + 1\right)e^{-\frac{t}{\tau_i}}\right)\frac{U_{ba}}{\tau_{max}} & t < \tau_{max} \\ \left(\left(1 + \frac{t - \tau_{max}}{\tau_i}\right)e^{-\frac{t-\tau_{max}}{\tau_i}} - \left(\frac{t}{T} + 1\right)e^{-\frac{t}{\tau_i}}\right)\frac{U_{ba}}{\tau_{max}} & t \geq \tau_{max} \end{cases} \quad (9)$$

The value of the time constant 336 $\tau_i$ in (9) is assumed to be equal to the time constant in (4). In fact, both rapid- and long-acting insulin take approximately the same time to achieve maximum effect, with the difference that rapid-acting insulin action peaks at this time, while long-acting insulin plateaus after this time for a duration $\tau_{max}$. The duration 358 represented by $\tau_{max}$ is set to be one day, i.e., $\tau_{max}$=1440 min. Equation (9) assumes that basal doses are always separated by the same time $\tau_{max}$.$I_{p0}$(t) can be determined from (9) by replacing $U_{ba}$ by B.

The solution of (8) for t<$\tau_{max}$ is expressed as equation (10)

$$G_p(t) = G_p(0) - S_i^{ba}(U_{ba} - B)\left(\frac{t - 2\tau_i}{\tau_{max}} + \frac{t + 2\tau_i}{\tau_{max}}e^{-\frac{t}{\tau_i}}\right) \quad (10)$$

Equation (10) demonstrates that glucose levels will remain constant after a basal dose 352 ($U_{ba}$) if it is equal to B, that is, the optimal basal insulin dose 354. Equation (10) also shows that an extra 1 unit of the long-acting insulin ($U_{ba}$–B=1 U) will decrease glucose level by $S_i^{ba}$ mmol/L after the insulin dose is completely absorbed at $\tau=\tau_{max}>>\tau_i$.

The basal dose effect calculator 360 is configured to: (i) receive an insulin basal dose 352; (ii) receive an estimated optimal basal insulin dose 354; (iii) receive a basal insulin sensitivity 356, a duration effect of the insulin basal dose 358; (iv) determine, based on the insulin basal dose 352, the estimated optimal basal insulin dose 354, the basal insulin sensitivity 356, the duration effect of the insulin basal dose 358, a second rate of insulin appearance 362 in the blood after the insulin basal dose 352.

The basal dose effect calculator 360 receives the insulin basal dose 352 administered to the diabetic user 205.

The basal dose effect calculator 360 receives the estimated optimal basal insulin dose 354. The estimated optimal basal insulin dose 354 may have been estimated by a physician of the diabetic user 205. The estimated optimal basal insulin dose 354 is an estimate of the basal dose which enables the diabetic user 205 to achieve satisfactory glycemia.

The basal dose effect calculator 360 receives the basal insulin sensitivity 356. The basal insulin sensitivity 356 is the sensitivity of the glucoregulatory system of the diabetic user 205 to basal insulin doses.

The basal dose effect calculator 360 receives the duration effect of the insulin basal dose 358.

The basal dose effect calculator 360 integrates the rate of glucose appearance from meals and disappearance due to insulin over time. In one or more embodiments, to obtain the second rate of insulin appearance 362, the basal dose effect calculator 360 subtracts the estimated optimal basal insulin dose 354 from the insulin bolus dose 332, and multiplies the result by the basal insulin sensitivity 356. The basal dose effect calculator 360 then divides the result by the squared sum of the TTP of carbohydrate absorption 304 plus one.

The basal dose effect calculator 360 obtains the second rate of insulin appearance 362 in the blood after an insulin basal dose 362 using equation (11):

$$I_p^{ba} = (U_{ba} - B) \cdot \frac{S_i^{ba}}{\tau_{max} \cdot s \cdot (\tau_i s + 1)^2} \quad (11)$$

Where $I_p^{ba}$(t) (U/min) is the second rate of insulin appearance 362 into the blood circulation, B is the estimated optimal basal insulin dose 354, $u_{ba}$ is the consumed meal 302, $s_i^{ba}$ is the basal insulin sensitivity 356, $\tau_{max}$ is the duration effect of insulin basal dose 362, and $\tau_i$ is the time-to-peak of insulin action 336.

The basal dose effect calculator 360 outputs the second rate of insulin appearance 362 in the blood after the insulin basal dose 352.

It will be appreciated that the meal effect calculator 320, the bolus dose effect calculator 340, the basal dose effect calculator 360 may be implemented as a single module or function.

Glucose Concentration Calculator

The glucose concentration predictor 380 is configured to: (i) receive the rate of meal glucose appearance 322, the first rate of insulin appearance 342 in the blood after an insulin bolus dose 332, and the second rate of insulin appearance 362 in the blood after an insulin basal dose 362; (ii)

determine, based on the rate of meal glucose appearance 342, the first rate of insulin appearance 342 in the blood after the insulin bolus dose 332, and the second rate of insulin appearance 362 in the blood after the insulin basal dose 352, a predicted plasma glucose concentration; and (iii) determine, based on the predicted plasma glucose concentration, a predicted interstitial glucose concentration 382.

The glucose concentration predictor 380 is a model of a glucose monitoring system of a patient. In one or more embodiments, the glucose concentration predictor 380 uses a diffusion model for predicting the plasma and interstitial glucose concentration of the patient based on inter alia the indication of the consumed meal 302, the insulin bolus dose 332, and the insulin basal dose 352.

The glucose concentration predictor 380 receives the rate of meal glucose appearance 322 from the meal effect calculator 320, the first rate of insulin appearance 342 in the blood after an insulin bolus dose 332 from the bolus dose effect calculator 340, and the second rate of insulin appearance 362 in the blood after the insulin basal dose 362 from the basal dose effect calculator 360. In one or more embodiments, the glucose concentration predictor 380 receives one or more of the rate of meal glucose appearance 322, the first rate of insulin appearance 342 in the blood, and the second rate of insulin appearance 362 in the blood from the database 220.

Glucose monitoring systems measure interstitial glucose concentrations $G_i(t)$ (mmol/L), which can be related to plasma glucose concentrations $G_p(t)$ through a diffusion model:

$$\frac{d}{dt}G_i(t) = -\frac{1}{\tau_s}G_i(t) + \frac{1}{\tau_s}G_p(t) \tag{12}$$

Since it is not possible to estimate $\tau_s$ without directly measuring plasma glucose, the value is fixed to $\tau_s=10$ min. The measured glucose is subjected to a sensor noise $\in(t)$. The noise is assumed to be additive and non-white, as follows:

$$G_m(t)=G_i(t)+\in(t)=G_i(t)+h(t)*e(t) \tag{13}$$

where e(t) is a white noise with zero mean and variance $\sigma^2$, and "*" denotes the convolution operator. The process h(t) is approximated in discrete time (t=kΔt) as a zero-mean, autoregressive model of order one:

$$\in_{k+1}=\alpha\in_k+e_k; 0 \le \alpha < 1 \tag{14}$$

The transfer function model linking the inputs $U_{ba}$, $U_{bo}$, and $U_m$ to the interstitial glucose concentration is given by:

$$G_i(s) = \frac{1}{\tau_s s + 1}\frac{1}{s}\left(\frac{K_m U_m}{(\tau_m s + 1)^2} - \frac{C_R K_m U_{bo}}{(\tau_i s + 1)^2} - \frac{S_i^{ba}\frac{U_{ba}-B}{\tau_{max}}}{s(\tau_i s + 1)^2}\right) \tag{15}$$

The glucose concentration predictor 380 calculates the predicted plasma glucose concentration.

The glucose concentration predictor 380 calculates the predicted plasma glucose concentration based on inter alia the rate of meal glucose appearance 322, the first rate of insulin appearance 342 in the blood after an insulin bolus dose 332, and the second rate of insulin appearance 362 in the blood after an insulin basal dose 352

It will be appreciated that the plasma glucose concentration and the interstitial glucose concentration are related through a diffusion model by a transfer-rate constant 372, $$G_i = G_p \cdot \frac{1}{\tau_s}.$$

The glucose concentration predictor 380 receives the transfer-rate constant 372 between plasma and interstitial glucose, which is represented by $\tau_s$ and expressed in minutes.

The glucose concentration predictor 380 calculates the predicted interstitial glucose concentration 382 based on the predicted plasma glucose concentration, i.e. based on inter alia the rate of meal glucose appearance 322, the first rate of insulin appearance 342 in the blood after an insulin bolus dose 332, the second rate of insulin appearance 362 in the blood after an insulin basal dose 352, and the transfer-rate constant 372.

In one or more embodiments, to obtain the predicted interstitial glucose concentration 382, the glucose concentration predictor 380 subtracts the first rate of insulin appearance 342 in the blood after the insulin bolus dose 332, and the second rate of insulin appearance 362 in the blood after the insulin basal dose 352 from the rate of meal glucose appearance 342. The glucose concentration predictor 380 divides the result by one plus the transfer-rate constant 372.

In one or more embodiments, the glucose concentration predictor 380 determines the predicted interstitial glucose concentration 382 by using equation (16):

$$G_i(s) = \frac{1}{\tau_s s + 1}\frac{1}{s}\left(R_a(s) - I_p^{bo}(s) - I_p^{ba}(s)\right) \tag{16}$$

Where $G_i$ is the predicted interstitial glucose concentration 382, $\tau_s$ is the transfer-rate constant 372, $R_a(t)$ is the rate of meal glucose appearance 322, $I_p^{bo}$ the first rate of insulin appearance 342 in the blood after the insulin bolus dose 332, and $I_p^{ba}$ is the second rate of insulin appearance 362 in the blood after the insulin basal dose 352. In one or more embodiments, $\tau_s=10$ minutes.

(16) In one or more embodiments, $\tau_s=10$ and $\tau_{max}=1440$ are assumed to be constant, parameters B, $S_i^{ba}$, $\tau_i$ and $K_m$ are estimated daily, and parameters $C_R$ and $\tau_m$ are estimated for each main meal consumed by the diabetic user 205.

The glucose concentration predictor 380 outputs the predicted interstitial glucose concentration 382. Additionally or alternatively, the glucose concentration predictor 380 outputs the predicted plasma glucose concentration.

Figure 4:
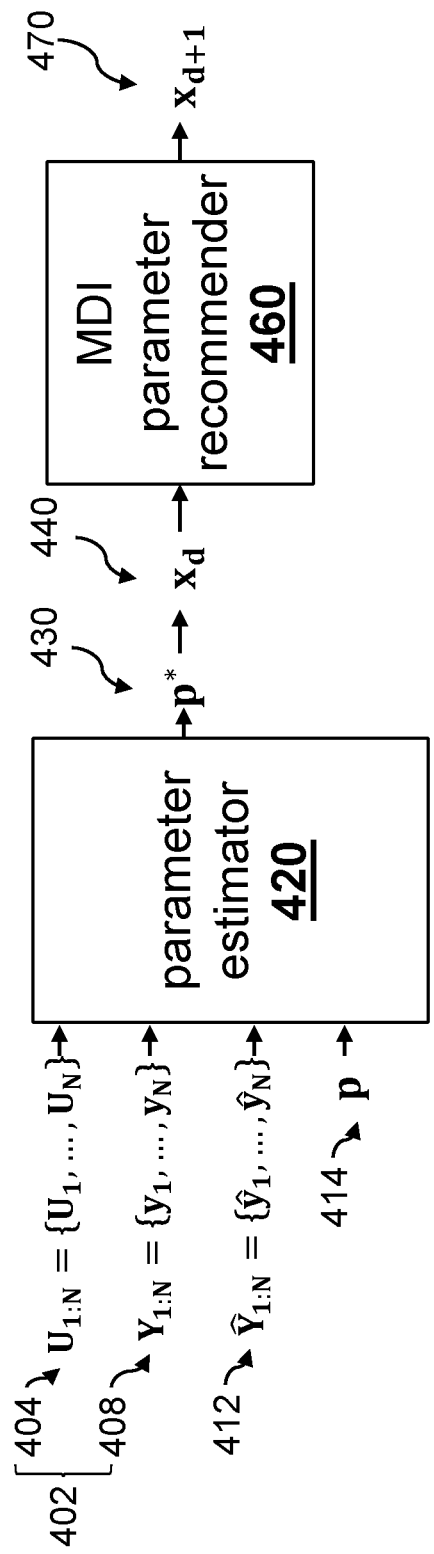
FIG. 4 depicts a schematic diagram of an optimal multiple daily injection (MDI) parameters determination procedure in accordance with one or more non-limiting embodiments of the present technology.

With reference to FIG. 4, there is depicted a schematic diagram of an optimal multiple daily injection (MDI) parameters determination procedure 400 in accordance with one or more non-limiting embodiments of the present technology.

Optimal MDI Therapy Parameters Determination Procedure

The optimal MDI therapy parameters determination procedure 400 is executed by the server 210. In one or more embodiments, the optimal MDI therapy parameters determination procedure is executed by the electronic device 100. The optimal MDI therapy parameters determination procedure 400 is executed after the glucose concentration prediction procedure 300.

The optimal MDI therapy parameters determination procedure 400 enables processing observed data including meal, insulin bolus and basal doses, and glucose concentration measurements and predicted glucose concentration to obtain values fora optimal MDI therapy parameters including optimal insulin basal dose and an optimal carbohydrate ratio values. The basal insulin dose and carbohydrate ratios are specific to each individual and are periodically adjusted to improve overall glycemic control.

In other words, the optimal MDI therapy parameters determination procedure 400 relates glucose concentrations to optimal MDI therapy parameters.

The optimal MDI therapy parameters determination procedure 400 is performed via the parameter estimator 420 and the MDI parameter recommender 460.

Parameter Estimator

The parameter estimator 420 is configured to: (i) receive a set of observed data 402; (ii) receive a set of glucose predictions 412; (iii) receive a set of model parameters 414; and (iii) calculate, using the set of observed data 402, the set of glucose predictions 412 and the set of model parameters 414, a set of maximum a posteriori (MAP) estimates 430.

The parameter estimator 420 receives the set of observed data 402. The set of observed data 402 includes a set of inputs 404 and a set of glucose measurements 408.

The set of inputs 404 includes: one or more insulin basal doses, one or more insulin bolus dose, and one or more consumed meals administered during a given period of time. The set of inputs 404 may be represented as a vector, where the elements represent the insulin basal dose, the insulin bolus dose and the ingested meals for a predetermined time period e.g., each 15 minutes, each hour, each day, each week and the like.

The set of observed data 402 includes a set of glucose measurements 408. The set of glucose measurements 408 includes interstitial glucose concentration measurements of the diabetic user 205 for the given time period. The set of glucose measurements 408 are actual interstitial glucose concentration measurements of the diabetic user 205 obtained as an example via blood glucose meter of the diabetic user 205. In one or more alternative embodiments, the set of glucose measurements 404 includes plasma glucose concentration measurements.

The parameter estimator 420 receives the set of glucose predictions 412. In one or more embodiments, the set of glucose predictions 412 is received from the database 220. In one or more other embodiments, one or more of the set of glucose predictions 412 is received after execution of the glucose concentration prediction procedure 300.

The set of glucose predictions 412 includes predicted interstitial glucose concentrations during the given period of time. Each predicted interstitial glucose concentration in the set of glucose predictions 412 is output by execution of the glucose concentration prediction procedure 300.

Using daily observed data $\mathcal{D}_d = \{Y_{1:N}, U_{1:N}\}$, the vector of parameter estimates p (which includes the desired MDI therapy parameters) can be estimated. By assuming a statistical approach and assuming that p is a random vector with probability distribution functions (PDF) denoted by $\mathcal{P}(p)$. At the end of each day, the posterior (or updated) PDF of the parameters p given data $\mathcal{D}_d$ (denoted by $\mathcal{P}(p|Y_{1:N}, U_{1:N})$) is related by Bayes' rule to the likelihood function $\mathcal{P}(Y_{1:N}|U_{1:N}, p)$ and the prior probability distribution $\mathcal{P}(p)$. The maximum a posteriori (MAP) estimate of p (denoted by p*) is the value for which $\mathcal{P}(p|Y_{1:N}, U_{1:N})$ attains its maximum.

$$p^* = \mathrm{argmax}_p \mathcal{P}(p|Y_{1:N}, U_{1:N}) \Leftrightarrow p^* = \mathrm{argmax}_p \mathcal{P}(Y_{1:N}|U_{1:N}, p)\mathcal{P}(p) \quad (17)$$

In one or more embodiments, the parameter estimator 420 incorporates constraints to equation (17) to ensure that the set of MAP estimates 430 represented by p* attains physiologically-plausible values. Constraints were incorporated in (15) to ensure that p* attains physiologically-plausible values. Hence, p* is obtained by solving the optimization problem:

$$p^* = \mathrm{argmin}_{p \in \mathcal{S}} J(p) + Q(p), \quad (18)$$

$$J(p) = \frac{1}{2\sigma^2}\|R_\alpha(Y_{1:N} - \hat{Y}_{1:N})\|^2 + N\log\sigma - \frac{1}{2}\log(1-\alpha^2) \quad (19)$$

$$Q(p) = \frac{1}{2}\|W^{-1}(\overline{p} - \overline{p}_0)\|^2 + tr(\log W) \quad (20)$$

where $\mathcal{S}$ is the domain of physiologically-plausible parameter values defined by the set of constraints in TABLE I, $R_\alpha$ is the inverse of the upper Cholesky decomposition of the noise covariance matrix, $\hat{Y}_{1:N} = \{\hat{y}_1, \ldots, \hat{y}_N\}$ is the set of glucose predictions 412, $\overline{p}$ is derived from p by replacing log-normally distributed parameters by their logarithms, W is the upper Cholesky decomposition of the covariance matrix of the prior distribution of $\overline{p}$, and $\overline{p}_0$ is the mean of the prior distribution of $\overline{p}$. The mean and the covariance (diagonal) matrix of $\overline{p}$ can be derived from the prior distributions in TABLE I. The mean of the prior distributions of MDI therapy parameters is set to the values used in the previous day.

The parameter estimator 420 receives or initializes the set of model parameters 414. The set of model parameters 414 include initial values of one or more parameters including initial values of MDI therapy parameters. Initial conditions are estimated for the given time period. As a non-limiting example, the given period of time may be a day. For subsequent days, the last state of the previous day is used as initial conditions.

The set of model parameters 414 includes: insulin sensitivity, the TTP of insulin action, carbohydrate sensitivity, the TTP of carbohydrate absorption, the noise standard deviation, and the noise autocorrelation. Each model parameter in the set of model parameters 414 is modeled by a respective distribution with respective constraints, which are detailed in Table I below.

TABLE I

Prior distributions of the set of model parameters 414 p. $N(\mu, \sigma^2)$ denotes the normal distribution with mean $\mu$ and variance $\sigma^2$.
$N_{log}(\mu_{log}, \sigma_{log}^2)$ denotes the log-normal distribution where $\mu_{log}$ and $\sigma_{log}^2$ are means and variance of the logarithmic values of the parameter.

| Parameter description | Distribution | Constraints |
|---|---|---|
| B: Optimal insulin basal dose | $B \sim N(U_{ba}, (0.1U_{ba})^2)$<br>$U_{ba}$ is the basal insulin | $B \in [0.25, 0.75]\mathrm{TDD}$. |

TABLE I-continued

Prior distributions of the set of model parameters 414 p. $N(\mu, \sigma^2)$ denotes the normal distribution with mean $\mu$ and variance $\sigma^2$. $N_{log}(\mu_{log}, \sigma_{log}^2)$ denotes the log-normal distribution where $\mu_{log}$ and $\sigma_{log}^2$ are means and variance of the logarithmic values of the parameter.

| Parameter description | Distribution | Constraints |
|---|---|---|
| $C_R$: Optimal carbohydrate ratio | used in a day. $C_R \sim N (C_{R0}, (0.2C_{R0})^2)$. $C_{R0}$ is the carbohydrate ratio used for a meal | $C_R \in [2, 50]$; |
| $s_i^{ba}$: Insulin sensitivity | $S_i^{ba} \sim N_{log}\left(\log\left(\frac{110}{TDD}\right), 0.005\right)$ | $S_i^{ba} \in [0.8, 1.3]\frac{110}{TDD} \cap$ $[0.9, 2.5]K_m C_R$ |
| $\tau_i$: Time-to-peak of insulin action | $\tau_i \sim N_{log}(\log(70), 0.01)$ | $\tau_i \in [45, 105]$ |
| $K_m$: Carbohydrate sensitivity | $K_m \sim N_{log}\left(\log\left(\frac{15}{w}\right), 0.03\right)$, where w is weight. | $K_m \in [0.5, 2.5]\frac{15}{w}$ |
| $\tau_m$: Time-to-peak of carbohydrate absorption | $\tau_m \sim N_{log}(\log(40), 0.02)$ | $\tau_m \in [15, 65]$ |
| $\sigma$: noise standard deviation | $\sigma \sim N_{log}(-1, 0.05)$ | $\log(\sigma) \in [-3, 1]$ |
| $\alpha$: noise autocorrelation | $\alpha \sim N(0.8, 0.05)$ | $\alpha \in [0.45, 0.95]$ |

In one or more embodiments, the set of model parameters 414 represented by p is a random vector with probability distribution functions (PDF) denoted by $\mathcal{P}$ (p). At the end of each day, the posterior (or updated) PDF of the set of model parameters 414 p given the set of observed data 402 represented by $\mathcal{D}_d$ (denoted by $\mathcal{P}$ (p|$Y_{1:N}$, $U_{1:N}$)), is related by Bayes' rule to the likelihood function $\mathcal{P}$ ($Y_{1:N}$|$U_{1:N}$, p) and the prior probability distribution $\mathcal{P}$ (p). The maximum a posteriori (MAP) estimate of p (denoted by p*) or the set of MAP estimates 430 is the value for which $\mathcal{P}$ (p|$Y_{1:N}$, $U_{1:N}$) attains its maximum.

The parameter estimator 420 determines the set of MAP estimates 430.

The parameter estimator 420 obtains the set of MAP estimates 430 by optimizing the probability distribution function of the set of model parameters 414 given the set of observed data 402.

In one or more embodiments, the set of MAP estimates 430 is obtained by optimizing equation (21):

$$p^* = \arg\max_p \mathcal{P}(p \mid Y_{1:N}, U_{1:N}) \Leftrightarrow p^* = \arg\max_p \mathcal{P}(Y_{1:N} \mid U_{1:N}, p)\mathcal{P}(p) \quad (21)$$

Where $Y_{1:N}$ is the set of glucose measurements 408, $U_{1:N}$ is the set of inputs 404, p is the set of model parameters 414, and p* is the set of MAP estimates 430.

In one or more embodiments, the parameter estimator 420 incorporates constraints to equation (15) to ensure that the set of MAP estimates 430 represented by p* attains physiologically-plausible values.

The parameter estimator 420 obtains the set of MAP estimates 430 by solving the optimization problem expressed as equations (16-18):

$$p^* = \mathrm{argmin}_{p \in S} \; J(p) + Q(p), \quad (18)$$

$$J(p) = \frac{1}{2\sigma^2}\left\|R_\alpha(Y_{1:N} - \hat{Y}_{1:N})\right\|^2 + N \log \sigma - \frac{1}{2}\log(1 - \alpha^2) \quad (19)$$

$$Q(p) = \frac{1}{2}\left\|W^{-1}(\bar{p} - \bar{p}_0)\right\|^2 + tr(\log W) \quad (20)$$

where $S$ is the domain of physiologically-plausible parameter values defined by the set of constraints in TABLE I, $R_\alpha$ is the inverse of the upper Cholesky decomposition of the noise covariance matrix, $\hat{Y}_{1:N} = \{\hat{y}_1, \ldots, \hat{y}_N\}$ is the set of glucose predictions 412, $\bar{p}$ is derived from p by replacing log-normally distributed parameters by their logarithms, W is the upper Cholesky decomposition of the covariance matrix of the prior distribution of $\bar{p}$, and $\bar{p}_0$ is the mean of the prior distribution of $\bar{p}$. The mean and the covariance (diagonal) matrix of p can be derived from the prior distributions in TABLE I. The mean of the prior distributions of MDI therapy parameters is set to the values used in the previous day.

It will be appreciated that equations (18-207) may be solved by the parameter estimator 420 using different techniques. In one or more embodiments, an analytical solution for the optimization problem of equation (21) may be obtained by differentiating the inverse Laplace function of equation (16-17). However it will be appreciated that obtaining the solution may be complex due to the nonlinear dependency of the temporal solution ($\hat{Y}_{1:N}$) on the set of model parameters 414 represented by p and due to the constraints in (21).

In one or more embodiments, the parameter estimator 420 obtains the set of MAP estimates 430 by alternating between gradient descent optimization and Monte-Carlo Markov Chain (MCMC) sampling.

First, the parameter estimator 420 executes a Metropolis-Hasting routine for exploring the parameters space and constructs a sample pool around the current best solution. This enables jumps in the parameters space unrelated to the gradient descent. Second, the sampling is halted, and multiple gradient descent optimizations are carried-on starting from randomly selected samples from the sample pool. This is done to benefit from the local convexity of (16) in some regions of the parameters space.

In one or more embodiments, the parameter estimator 420 is implemented via PSEUDOCODE 1:

PSEUDOCODE 1

```
While number of samples < N_tot
    Enter Metropolis-Hasting routine
        Randomly generate m initial samples around p*.
        For each initial sample p_m (parallel loop)
            For iterator less than B + N/m/T
                For x_i in the sample p_m
                    x_i = x_i + a random walk.
                    Create a new sample p_m^New with changed x_i
                    Compute the acceptance ratio α = J(p_m^New)/J(p^m)
                    If β drawn from the standard uniform distribution is ≥ log α
                        save new sample p_m^New.
        Discard the burn-in samples (B).
        Combine the m chains.
        Down-sample using the thinning coefficient (T).
        Add new samples (N) to S
        In S, discard samples with a cost far from the minimal cost.
    Set p* to the sample with minimum cost in S.
    Enter Gradient Descent routine
        While convergence criteria are not attained
            Uniformly choose m sample from S.
            For each sample p_m (parallel loop)
                Run gradient descent starting from p_m.
                Save sample p_m^New and cost resulting from gradient descent.
            If in the new m samples, a better cost value than p* is achieved
                Set new optimum p* = p_m^New.
            If p* did not change or cost function stopped decreasing
                Convergence criterion is met.
Return p*
```

It will be appreciated that due to the probabilistic aspect of MCMC, a big enough sample size must be chosen to ensure reproducibility of the algorithm With a sample size of $N_{tot}=128$, parameter estimates only differed by a coefficient of variation of ~0.01%.

After convergence, the parameter estimator 420 obtains the set of MAP estimates 430 p* and a pool of samples. The parameter estimator 420 uses the pool of samples to approximate the expectation $\mathbb{E}$ [p*] and the uncertainty of the set of MAP estimates 430. The set of MAP estimates 430 are output for a predetermined time period. As a non-limiting example, the set of MAP estimates 430 may be obtained for a day.

MDI Parameter Recommendation

In MDI therapy, insulin doses are determined by the therapy parameters: daily basal dose 354 represented by B (U) and carbohydrate ratios 334 represented by $C_R$ (g/U). Let $X_d$ be a therapy parameter used on day d. Let $\hat{X}_d$ be a random variable describing the unknown optimal therapy parameter on day d, and $\mathcal{P}(\hat{X}_d | \mathcal{D}_d)$ be the probability density function of $\hat{X}_d$ conditioned on the observed data $\mathcal{D}_d$. The data set, $\mathcal{D}_d = \{Y_{1:N}, U_{1:N}\}$, is observed each day and consists of measured glucose levels $Y_{1:N}=\{y_1, \ldots, y_N\}$ and inputs $U_{1:N}=\{U_1, \ldots, U_N\}$ comprising the insulin basal dose $U_{ba}$, the insulin boluses $U_{bo}$, and the meals $U_m$. Every day, a new MDI therapy parameter $(X_{d+1})$ is determined as:

$$X_{d+1} = X_d + \phi(\eta(\mathbb{E}[\hat{X}_d] - X_d)) \quad (22)$$

where $\mathbb{E}[\hat{X}_d]$ is the expected value of $\hat{X}_d$, η is a coefficient between 0 and 1, and $\phi(\cdot)$ is a saturation function defined as:

$$\phi(x) = \begin{cases} 0 & |x| < \delta x_{min} \\ \frac{x}{|x|} \delta x_{max} & |x| \geq \delta x_{max}) \\ x & \text{otherwise} \end{cases} \quad (23)$$

where $\delta x_{min}$ and $\delta x_{max}$ are the minimum and maximum changes allowed for parameter x, respectively.

The MDI parameter recommender 460 is configured to: (i) receive the set of MAP estimates 430 including a set of MDI therapy parameters 440; and (ii) determine, based on the set of MDI therapy parameters 440, a new set of MDI therapy parameters 470.

The MDI parameter recommender 460 receives the set of MAP estimates 430 (represented by p*) and the pool of samples, the expectation $\mathbb{E}$ [p*] and the uncertainty of the set of MAP estimates 430.

The MDI parameter recommender 460 selects the set of MDI therapy parameters 440 (represented by $X_d$) from the set of MAP estimates 430 (represented by p*). The set of MDI therapy parameters 440 is a subset of the set of MAP estimates 430.

The set of MDI therapy parameters 440 includes one or more of: an optimal insulin basal dose (represented by B) and an optimal carbohydrate ratio (represented by $C_R$).

The MDI parameter recommender 460 determines the expected value of the set of MDI therapy parameters 440, represented by $\mathbb{E}[\hat{X}_d]$.

The MDI parameter recommender 460 determines a coefficient η which may be regarded as a learning rate of the update rule in (22). The coefficient describes the confidence in the parameters estimates. The confidence in the parameters estimates is explained by the coefficient of variation (CV) of the set of MDI therapy parameters 440 and local mean absolute error (MAE) of the difference between the set of glucose measurements 408 and the set of glucose predictions 412 resulting from the fit.

In one or more embodiments, the MDI parameter recommender 460 determines the coefficient of variation (CV) of the set of MDI therapy parameters estimates 440 ($\hat{X}_d$) expressed as equation (24):

$$CV = \frac{\sqrt{\mathbb{E}\left[(\hat{X}_d - \mathbb{E}[\hat{X}_d])^2\right]}}{\mathbb{E}[\hat{X}_d]} \quad (24)$$

In one or more embodiments, the MDI parameter recommender 460 determines the local mean absolute error (MAE) of the difference between the set of glucose measurements 408 and the set of glucose predictions 412 resulting from the fit expressed as equation (25):

$$MAE = \frac{1}{L} \sum_{k=M}^{M+L-1} |y_k - \hat{y}_k| \quad (25)$$

where L is a time window, and M is a time characterizing the set of MDI therapy parameters estimates 440 $X_d$. For instance, errors in glucose predictions after a meal are used to compute a local MAE for the carbohydrate ratio used for the meal.

The MDI parameter recommender 460 determines the coefficient η based on the CV and the MAE. In one or more embodiments, the MDI parameter recommender 460 determines the coefficient by combining the CV and the MAE, which is expressed as equation (26):

$$\eta = \frac{1}{1 + \frac{MAE}{MAE_{half}}} \cdot \frac{1}{1 + \frac{CV}{CV_{half}}} \tag{26}$$

where $MAE_{half}$ and $CV_{half}$ are tuning parameters. The values may be set to tune the aggressiveness of the algorithm. As a non-limiting example, $MAE_{half}$=1.5 mmol/L for all therapy parameters, $CV_{half}$=0.03 for basal insulin, and $CV_{half}$=0.05 for carbohydrate ratios The coefficient η depends on (i) the reliability of the MDI therapy parameter estimates and (ii) the quality of the data $\mathfrak{D}_d$. The greater the confidence in the estimate, the larger the value of η should be. When η=1, the new therapy parameter in day d+1 is set to $\mathbb{E}[\hat{X}_d]$. When η=0, the therapy parameter is kept unchanged.

The MDI parameter recommender 460 determines the new set of MDI therapy parameters 470 for the next predetermined time period, represented as $X_{d+1}$, by using equation (22):

$$X_{d+1} = X_d + \phi(\eta(\mathbb{E}[\hat{X}_d] - X_d)) \tag{22}$$

where $\mathbb{E}[\hat{X}_d]$ is the expected value of $\hat{X}_d$, η is a coefficient between 0 and 1, and $\phi(\bullet)$ is a function defined as:

$$\phi(x) = \begin{cases} 0 & |x| < \delta x_{min} \\ \frac{x}{|x|} \delta x_{max} & |x| \geq \delta x_{max} \\ x & \text{otherwise} \end{cases} \tag{23}$$

where $\delta x_{min}$ and $\delta x_{max}$ are the minimum and maximum changes allowed for parameter x, respectively.

In one or more embodiments, the MDI parameter recommender 460 is configured to apply a set of rules on the new set of MDI therapy parameters 470 to prevent outputting unsafe recommendations.

As a non-limiting example, if one had hypoglycemia after the lunch meal, a rule prevents recommending a smaller carbohydrate ratio (i.e., more insulin) for the lunch meal.

The MDI parameter recommender 460 outputs the new set of MDI therapy parameters 470.

The new set of MDI therapy parameters 470 may then be used for administering basal insulin to the diabetic user 250 for achieving satisfactory glycemia.

Method Description

Figure 5:
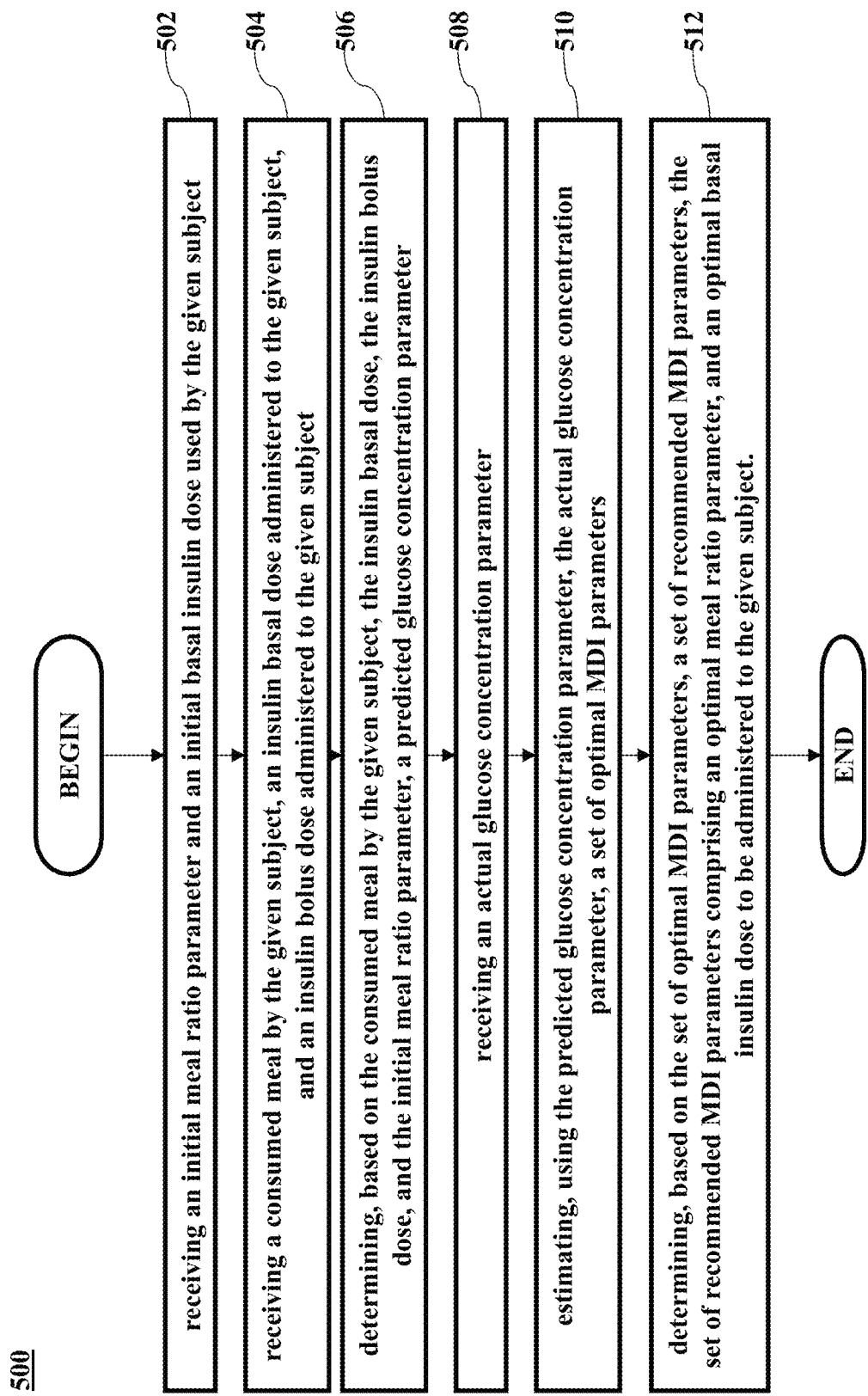
FIG. 5 depicts a flow chart of a method for determining optimal MDI therapy parameters for a given subject in accordance with one or more non-limiting embodiments of the present technology.

FIG. 5 depicts a flowchart of a method 500 of determining an optimal set of MDI therapy parameters, the method 500 being executed in accordance with one or more non-limiting embodiments of the present technology.

The server 210 comprises a processing unit such as the processor 110 and/or the GPU 111 and a non-transitory computer readable storage medium operatively connected to the processing unit, such as the solid-state drive 120 and/or the random-access memory 130, which stores computer-readable instructions. The processor 110 and/or the GPU 111, upon executing the computer-readable instructions, is configured to execute the method 500.

In one or more embodiments, the method 500 is executed by the electronic device 100 which comprises a processing unit such as the processor 110 and/or the GPU 111 operatively connected to a non-transitory computer readable storage medium such as the solid-state drive 120 and/or the random-access memory 130 storing computer-readable instructions. The processor 110 and/or the GPU 11, upon executing the computer-readable instructions, is configured to execute the method 500.

The method 500 begins at processing step 502.

According to processing step 502, the processor 110 receives an initial meal ratio parameter in the form of an initial estimated carbohydrate ratio 334, and an estimated optimal basal insulin dose 354. The initial estimated carbohydrate ratio 334, and an estimated optimal basal insulin dose 354 may have been chosen by the user's 205 physician for example.

According to processing step 504, the processor 110 receives the indication of the consumed meal 302, the insulin bolus dose 332, and the insulin basal dose 352 administered to the diabetic user 205. It will be appreciated that each of the indication of the consumed meal 302, the insulin bolus dose 332, and the insulin basal dose 352 may be received at the same time or at different times. In one or more embodiments, the indication of the consumed meal 302, the insulin bolus dose 332, and the insulin basal dose 352 may be received from an electronic device 100 of the diabetic user 205.

It will be appreciated that processing step 504 may be executed prior to processing step 502.

According to processing step 506, the processor 110 determines, based on the indication of the consumed meal 302, the insulin bolus dose 332, the insulin basal dose 352, the initial estimated carbohydrate ratio 334, and the estimated optimal basal insulin dose 354, a predicted glucose concentration parameter.

In one or more embodiments, to obtain the predicted glucose concentration parameter, the processor 110 determines: a rate of meal glucose appearance 322 in the blood after the ingested meal 302, a first rate of insulin appearance 342 in the blood after an insulin bolus dose 332, and second rate of insulin appearance 362 in the blood after an insulin basal dose 362.

In one or more embodiments, to obtain a rate of meal glucose appearance 322 in the blood after the ingested meal 302, the processor 110 receives a carbohydrate sensitivity 308, a time-to-peak (TTP) of carbohydrate absorption 304, and determines, based on the consumed meal 302, the carbohydrate sensitivity 308, the TTP of carbohydrate absorption 304, a rate of meal glucose appearance 322 in the blood after the ingested meal 302.

In one or more embodiments, to obtain the first rate of insulin appearance 342 in the blood after an insulin bolus dose 332, the processor 110 receives the carbohydrate sensitivity 308, and a time-to-peak of insulin action 336. The processor 110 determines, based on the insulin bolus dose 332, the initial estimated carbohydrate ratio 334, the carbohydrate sensitivity 308, the TTP of insulin action 336, the first rate of insulin appearance 342 in the blood after an insulin bolus dose 332.

In one or more embodiments, to obtain the second rate of insulin appearance 365, the processor 110 receives a basal insulin sensitivity 356, and a duration effect of the insulin basal dose 358. The processor 110 determines, based on the insulin basal dose 358, the estimated optimal basal insulin dose 354, the basal insulin sensitivity 356, and the duration effect of the insulin basal dose 358, the second rate of insulin appearance 362 in the blood after an insulin basal dose 362.

The processor 110 determines, based on the rate of meal glucose appearance 342, the first rate of insulin appearance 342 in the blood after an insulin bolus dose 332, and the second rate of insulin appearance 362 in the blood after an insulin basal dose 352, the predicted glucose concentration parameter. In one or more embodiments, the predicted glucose concentration parameter is the predicted plasma glucose concentration. In one or more other embodiments, the processor 110 determines a predicted interstitial glucose concentration 382 as the predicted plasma glucose concentration parameter based on the predicted plasma glucose concentration.

According to processing step 508, the processor 110 receives an actual glucose concentration parameter in the form of a set of glucose measurements 408. The set of glucose measurements 408 includes interstitial glucose concentration measurements of the diabetic user 205 for the given time period.

It will be appreciated that processing step 508 may be executed prior to processing step 506.

The processor 110 receives a set of inputs 404 including one or more insulin basal doses, one or more insulin bolus dose, and one or more consumed meals for the given time period.

According to processing step 510, the processor 110 estimates a set of model parameters using the predicted glucose concentration parameter, the measured glucose concentration parameter.

The estimated set of model parameters comprises a set of maximum a posteriori (MAP) estimates 430.

In one or more embodiments, the processor 110 obtains the set of MAP estimates 430 by alternating between gradient descent optimization and Monte-Carlo Markov Chain (MCMC) sampling.

First, the processor 110 may execute a Metropolis-Hasting routine for exploring the parameters space and constructs a sample pool around the current best solution. Second, the processor 110 halts sampling and carries multiple gradient descent optimizations starting from randomly selected samples from the sample pool. The processor 110 obtains the set of MAP estimates 430 and a pool of samples. The parameter estimator 420 uses the pool of samples to approximate the expectation and the uncertainty of the set of MAP estimates 430

The processor 110 obtains the set of multiple daily injection (MDI) therapy parameters 440 from the set of MAP estimates 430. The set of MDI therapy parameters 440 includes an optimal insulin basal dose and an optimal carbohydrate ratio.

According to processing step 512, the processor 110 determines, based on the set of multiple daily injection (MDI) therapy parameters 440 for the time period, a new set of MDI therapy parameters 470 for the next time period.

In one or more embodiments, the processor 110 determines the expected value of the set of MDI therapy parameters 440, and determines coefficient of variation (CV) of the set of MDI therapy parameters 440 and local mean absolute error (MAE) of the difference between the set of glucose measurements 408 and the set of glucose predictions 412.

The processor 110 determines a learning rate coefficient based on the CV and the MAE.

The processor 110 determines a new set of MDI therapy parameters 470 for the next time period based on the set of MDI therapy parameters 440, the expected value of the set of MDI therapy parameters 440, and the learning rate coefficient.

In one or more embodiments, processing steps 506, 508 and 519 may be executed together.

The method 500 ends.

It will be appreciated that not all technical effects mentioned herein need to be enjoyed in each and every embodiment of the present technology. For example, one or more embodiments of the present technology may be implemented without the user enjoying some of these technical effects, while other non-limiting embodiments may be implemented with the user enjoying other technical effects or none at all.

Experimental Results

The present approach assumes that there exists a set of optimal therapy parameters for each day that will provide optimal glycemic control: (i) after an insulin bolus, glucose levels return to initial glucose values, (ii) after an insulin basal dose, in absence of other perturbations, glucose levels stay constant throughout the day. The proposed method estimates this optimal value, then gradually converges to it.

Since optimal therapy parameters can be different from day-to-day, in theory, this method will converge to the average daily optimal therapy parameter. Still, people with type 1 diabetes present considerable day-to-day variability, and the optimal therapy parameter might differ considerably between consecutive days. To avoid oscillations and improve the robustness, multiple recommendations $X_d$ are averaged over a period of days $P_d$ and only make an update each $P_d$ days.

Method Validation

The insulin dose optimization algorithm is composed of two steps: a parameters estimation step and a dose recommendation step. The parameter estimation step was evaluated using clinical data to validate (i) the ability of the model to fit complex real data, and (ii) the physiological plausibility of the estimated parameters. The dosing recommendation step was evaluated using 60-day simulations on 100 virtual patients (VP) and compared to a baseline R2R algorithm. Furthermore, data from a 6-day clinical experiment in adolescent was used to demonstrate the feasibility of the present algorithm.

Baseline R2R Algorithm

Results from the R2R algorithm proposed by Toffanin et al. have been reproduced for comparison purposes. This algorithm was designed for a closed-loop system implemented with insulin pumps. The algorithm was modified to be suited for MDI therapy by assuming one basal dose and three carbohydrate ratios. The algorithm gains were kept the same as the ones published. This R2R algorithm only uses glucose information and the time of the insulin boluses.

Simulation Environment

A simulation environment was used for algorithm assessment. This simulation environment implemented VP based on Hovorka's model. Model parameters were sampled from a prior log-normal distribution with a mean taken from Wilinska et al. and parameter correlations from healthy individual data. Day-to-day glucose variability was implemented by making parameters oscillate periodically, with a random frequency and phase for each day as described in, and by adding daily random glucose and insulin fluxes representing unexplained changes in plasma glucose and plasma insulin. Variability in meal absorption was implemented by modeling slow and fast carbohydrate absorption rates, and by varying the time-to-peak of carbohydrate absorption for each meal. The simulation includes noise in glucose measurements with a coefficient of variation of 7% and a correlation of 80%. Random carbohydrate counting errors with a coefficient of variation of 20% were included.

All VP possessed a unique and optimal basal dose and carbohydrate ratio. The optimal basal dose was computed from differential equations by assuming that it will keep glucose levels constant during fasting conditions. The optimal carbohydrate ratio was determined by running an 8-hour simulation with a fixed meal and different values of boluses and checking that only one value of carbohydrate ratio can bring back glucose to its value before meal consumption. VP were sampled such as the resulting MDI therapy parameter are representative of an adult T1D population.

The simulation environment was validated by reproducing similar glucose outcomes from a clinical experiment s Clinical Data Clinical data of 150 days (10 days×15 participant) was used for validation. The data was collected from 15 adolescents, including 8 females, in a diabetes camp: age 12.5 (SD, 3.7), TDD 0.8 U/Kg (SD, 0.3), and HbA1c 8.7% (SD, 1.9). Each participant wore a Freestyle Libre glucose sensor (Abbott Diabetes Care). The Freestyle Libre is a glucose monitoring system that provides a value of interstitial glucose every 15 min. Participants had three main meals every day, whose content changed between days and between participants. Physical activities were common throughout the camp, and snacks were permitted and not accompanied by insulin boluses. Treated hypoglycemia events and the amount of carbohydrates used for hypoglycemia treatments were recorded. The clinical data was characterized by a mean glucose level of 11.2 mmol/L (SD, 3.1) and a coefficient of variation of 38% (SD, 12).

Model Fit Assessment

The goodness of the model fit was assessed by analysis of residuals. Weighted residuals (WR) are defined at each time k as the ratio between the residuals and estimated noise standard deviation:

$$WR_k = \frac{y_k - \hat{y}_k}{\sigma} \quad (2)$$

The proportion of variance explained (PVE) is defined by comparing the sum of squared residuals to the data variance:

$$PVE = 1 - \frac{\sum_{k=1}^{N}(y_k - \hat{y}_k)^2}{\sum_{k=1}^{N}(y_k - \bar{y})^2}; \bar{y} = \frac{1}{N}\sum_{k=1}^{N} y_k \quad (16)$$

Root-mean-squared-error (RMSE) is defined as:

$$RMSE = \sqrt{\frac{1}{N}\sum_{k=1}^{N}(y_k - \hat{y}_k)^2} \quad (24)$$

Runs test were performed to ascertain the randomness of residuals. Results are reported as median and interquartile range (IQR) or mean and standard deviation (SD).

Results

Assessment of Parameter Estimates Using Clinical Data

A fit was performed to the 150 days of clinical data in 15 participants using MDI therapy, and model parameters were estimated. The data consisted of measured glucose, delivered insulin doses, ingested meals (only main meals, snacks were not provided to the algorithm), and hypoglycemia treatments. Parameters for each day were estimated separately; however, each set of an individual's data (10 days) was fitted consecutively, such as the last state of the previous day is used as an initial condition in the following day.

Figure 6:
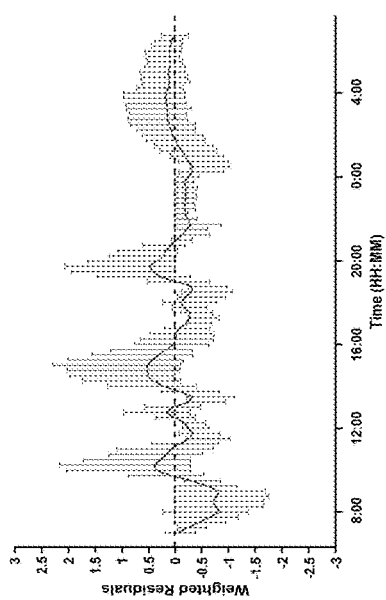
FIG. 6 depicts a plot of median and interquartile range of weighted residuals of the model fit to clinical data consisting of 150 days (10 days×15 participants) in accordance with one or more non-limiting embodiments of the present technology.

FIG. 6 shows the median and interquartile range of the weighted residuals. Overall, the obtained residuals confirm that the proposed model provides enough flexibility to accommodate complex real-life glucose patterns. All residuals passed the Runs test for randomness. The bias in the weighted residuals was −0.06 (IQR, −0.15-0.06), and the corresponding RMSE was 1.75 mmol/L (SD, 0.8). During the night, the RMSE was 1.26 mmol/L (SD, 0.94), while during the day, it was 1.9 mmol/L (SD, 0.85). The PVE was 77.3% (IQR, 64.6-87.7). The weighted residuals increased at mealtimes (8:00, 12:00, and 18:00). This might be caused by two reasons. First, the algorithm assumed that the meals were eaten instantaneously, while, in reality, participants spent time collecting and eating their meals, occasionally multiple times, while participating in various activities. Second, participants had snacks after meals, which were not entered into the algorithm.

Figure 7:
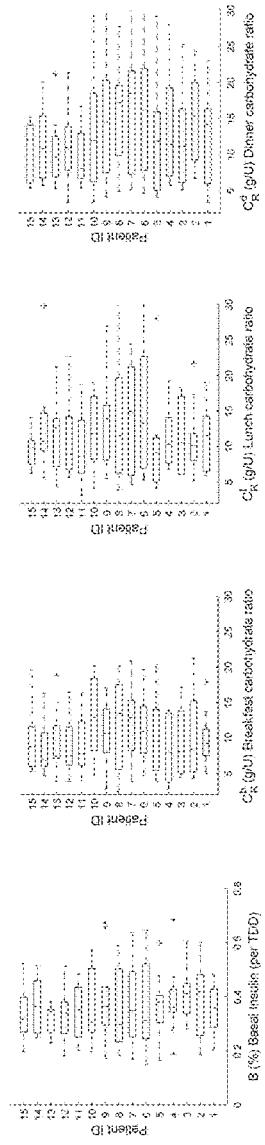
FIG. 7 depicts plots of maximum a posteriori (MAP) estimate performed on clinical data consisting of 150 days (10 days×15 participants), where parameters for each participant are represented by the blue horizontal box plots, and Basal insulin is presented as a percentage of TDD. Insulin sensitivity ($S_i$) and sitivity ($K_m$) are normalized by multiplying by and weight, respectively.
Figure 7:
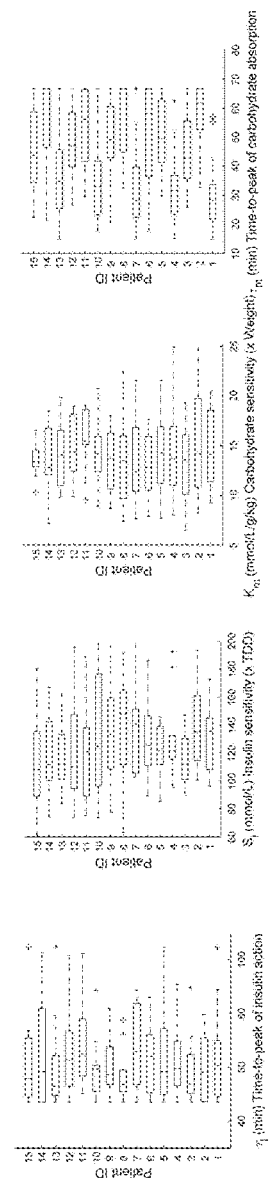

FIG. 7 shows the parameter estimates for the 15 participants over 10 days. Each participant's parameters are presented as a boxplot showing intra-individual variability between days. Coefficient of variation of all estimated parameters (n=1492) was 4.5% (IQR, 2.8-7.0); the maximum coefficient of variation was 63%. Parameter estimates were all physiologically plausible. The average estimated carbohydrate ratio was 10.8 g/U (IQR, 6.8-15.2). Breakfast carbohydrate ratio was 9.1 g/U (IQR, 6.3-13.9) with a coefficient of variation between days of 37% (IQR, 28-44). Lunch carbohydrate ratio was 10.5 g/U (IQR, 7.0-14.9), with a coefficient of variation between days of 53% (IQR, 44-69). Dinner carbohydrate ratio was 12.7 g/U (IQR, 6.9-17.6) with a coefficient of variation between days of 53% (IQR, 42-55). The observed variations in estimated carbohydrate ratios between days can be explained by differences in fat and protein contents between meals, as well as differences in physical activities and snacks after the meals. Basal insulin represented 35% (IQR, 27-43) of total daily insulin dose. In absolute value, basal insulin was 11.0 U (IQR, 7.5-18.0). Insulin sensitivity was 4.4 mmol/L/U (SD, 2.5) with a coefficient of variation between days of 28% (IQR, 23-31).

In order to evaluate the effect of the constraints on parameter estimates, the same experiment was reproduced but without constraints (results not shown). 97.2% of parameter estimates were within the constraints.

Simulation of Day-to-Day Insulin Doses Optimization

100 VP were created using the simulation environment described in section II-D-2. Each VP consumed three main meals per day. Meals had random amounts of carbohydrates and were consumed at random times, inside pre-set intervals. For instance, lunch was consumed between 11:30 and 13:00, and the amount was between 60 g and 100 g of carbohydrates. Up to two snacks (afternoon and bedtime) were consumed randomly, and their information was not provided to the algorithm. The total amount of carbohydrates consumed during a day was restricted to be between 140 g and 280 g. Only the main meals were accompanied by insulin boluses. The bolus doses were computed using the current glucose level and the carbohydrates that were counted by the VP (values were different from the true values because of the random counting errors). A correction bolus was delivered if glucose values stayed above 18 mmol/L for more than an hour. VP had one insulin basal dose at the start of each day (7:00). They consumed carbohydrates treatment (values were random around 16 g) when blood glucose went below 2.8 mmol/L or when sensor glucose stayed below 3.9 mmol/L for more than 60 min. Sensor glucose values were sampled every 15 minutes.

The initial MDI therapy parameters in day 1 were selected to differ by 25-75% from the optimal MDI therapy parameters and such as the resulting TDD is no more than 25% of their usual TDD. This simulates situations where insulin boluses are covered by basal insulin and vice-versa. Each day, the algorithm provided new therapy parameters that were applied in the following day. Parameters $MAE_{half}$ and $CV_{half}$ were not adjusted for this specific simulation; instead, they were kept to values used during the clinical experiment (II.D.3).

Figure 8:
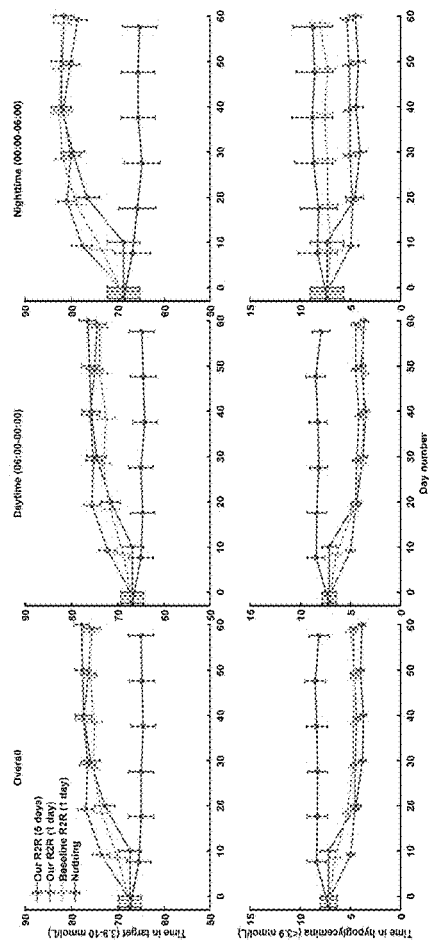
FIG. 8 depicts plots of time in target and time in hypoglycemia for 100 VP in 30-day simulations of daily therapy parameters adjustments using the algorithm of the present technology, baseline run-to-run algorithm, or no adjustments. Data point represent mean values for 100 VP. Error bars represent the 95% confidence interval, where the length of each bar is $1.96/(\sqrt{n})$ (n=100) multiplied by the standard deviation in accordance with one or more non-limiting embodiments of the present technology.

FIG. 8 shows the changes in glycemic outcomes for 100 VP over 60 days between (i) adjustments with the present algorithm but only the average recommendation of $P_d=5$ consecutive days is applied in the fifth day; (ii) daily adjustments with the present algorithm ($P_d=1$); (iii) daily adjustments with the baseline R2R algorithm; (iv) no adjustment. The same VP underwent the four arms, and, for each VP, daily variabilities and meals were the same between arms. Glycemic outcomes (time in target (3.9-10 mmol/L) and time in hypoglycemia (<3.9 mmol/L)) were computed over the last 10 days of the simulation.

Figure 9:
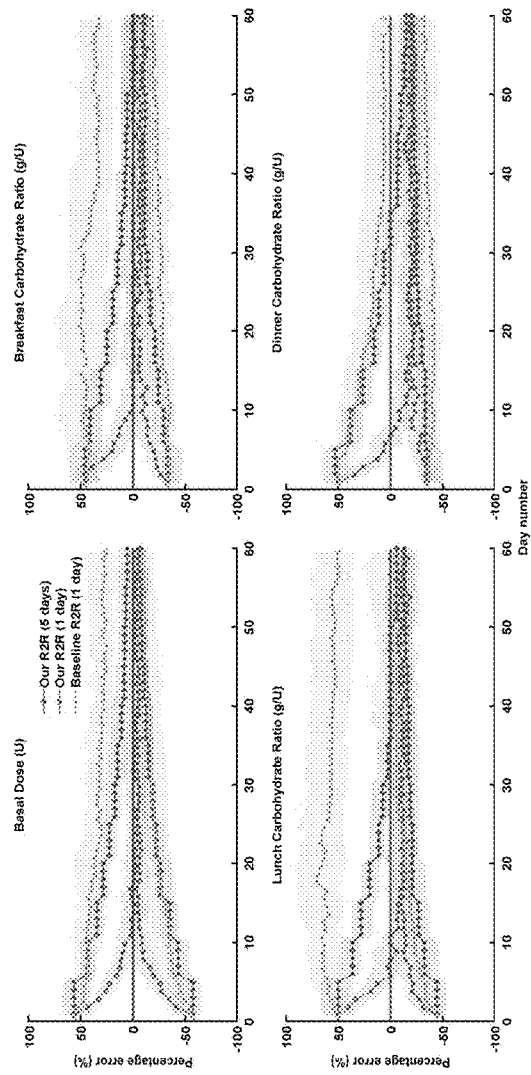
FIG. 9 depicts plots of daily percentage error in therapy parameters. Errors are calculated as a percentage difference from optimal parameter where hard line represents the median values, and patch represents the 25%-75% percentile of parameter errors in accordance with one or more non-limiting embodiments of the present technology.
Figure 10:
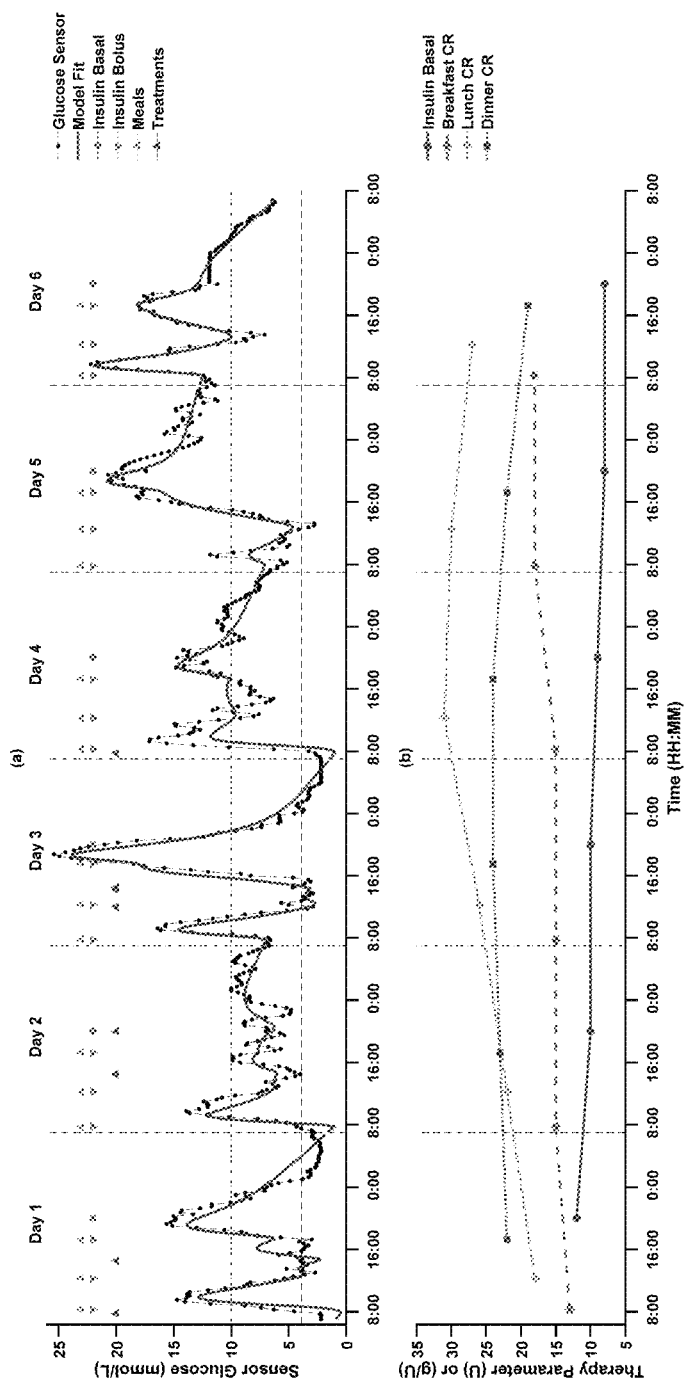
FIG. 10 depicts plots of: (a) sample model fit of glucose sensor data, where the black circles are sensor measurements, and the red solid line represents the model fit; (b) daily therapy parameters recommendations from the algorithm of the present technology, where the suggested recommendations were applied each day, and where CR stands for carbohydrate ratio.

FIG. 9 shows an example of a 6-day optimization on one of the participants in the clinical experiment. Analysis of day-to-day recommendations can be used to conceptually validate the algorithm's behavior. Overall, the algorithm recommendations were logical from day to day:

Day 1: A hypoglycemia event occurred after lunch causing the algorithm to suggest an increase in carbohydrate ratios (decreasing insulin boluses). At night, a pronounced hypoglycemia event is observed, causing the algorithm to recommend a decrease in basal insulin.

Day 2: Even though there was an increase in carbohydrate ratios compared to day 1, two post-meal hypoglycemia were still observed after lunch and dinner. The algorithm recommended a further increase in lunch carbohydrate ratio. There was no change in basal insulin dose. Overall day 2 was characterized by an increased time spent in glucose target range.

Day 3: Despite delivering less insulin than previous days, there were multiple hypoglycemia events (afternoon and during night) and a pronounced hyperglycemia in the middle of the day. The hyperglycemia was caused by an over-treatment of hypoglycemia, and the following hypoglycemia might have been caused by an overcorrection of hyperglycemia. Based on day 3 data, the algorithm recommended further decrease in insulin doses.

Day 4 to 6: There were fewer hypoglycemia events but there was hyperglycemia after lunch and dinner. The algorithm slowly increased insulin doses after lunch and dinner by decreasing their carbohydrate ratios. Because of the decreasing trend of glucose levels during the nights, the algorithm did not increase the basal insulin dose, even if they spent most of the night in hyperglycemia.

Discussion

People with T1D live with life-long burden of making important decisions about their daily insulin doses. Therefore, an effective decision support system could contribute to improving their quality of life. The proposed algorithm is a step forward towards developing a decision support system for people with T1D using MDI therapy.

The present approach utilizes an R2R update rule, yet, it stands out by that it combines glucose data with insulin and meal data via a model to guide the run-to-run algorithm. The model is characterized by (i) the separation of the basal and bolus insulin effects on glucose and (ii) the different sensitivities of insulin boluses for each meal. This provides a way to model (i) different carbohydrate ratios depending on the time of the meal, and (ii) the variation in insulin sensitivity depending on the state of fasting or postprandial. the present results showed that the model fit real-world data with different carbohydrate ratios while estimating independently insulin sensitivity for the basal insulin.

Through the model structure, the basal insulin dose ensures stable glucose during fasting conditions (Equation (10)) while the optimal carbohydrate ratios ensure that glucose levels return to their premeal values after 4-5 hours (Equation (5)). This model structure imposes the application of known guidelines for adjusting insulin doses. For example, when glucose levels are high throughout the night but stable, equation (5) will impose a change in the dinner bolus dose by changing the optimal carbohydrate ratio estimate instead of Compared to no adjustments, the glycemic outcomes in the last 10 days of the 60 days experiment were improved by using the present algorithm with $P_d=5$ (time in target increased from 64.2% (SD, 13.8) to 77.0% (SD, 8.8, p<0.01); time in hypoglycemia was decreased from 8.1% (SD, 5.0) to 3.8% (SD, 1.7, p<0.01)). This improvement was superior compared to the same algorithm but with $P_d=1$ (time in target 74.8% (SD, 9.3, p<0.01); time in hypoglycemia 4.7% (SD, 1.8, p<0.01)), and compared to the baseline R2R ($P_d=1$) (time in target 75.0% (SD, 8.2, p<0.01); time in hypoglycemia 4.9% (SD, 2.4, p<0.01)).

With $P_d=1$, the present R2R showed similar overall outcomes to baseline R2R (time in target p=0.75; time in hypoglycemia p=0.15). However, with baseline R2R, the night hypoglycemia (8.1% (SD, 4.7)) was not improved compared to no adjustments (8.5% (SD, 9.6%), p=0.6), as opposite to the present algorithm ($P_d=1$) (5.4% (SD, 3.1, p<0.01)).

A slight deterioration of glycemic outcomes starting at day 40 is observed with ($P_d=1$). This might be related to day-to-day variabilities: when errors in MDI therapy were large R2R quickly adjusted for the errors, but when the errors became small the algorithm started reacting to noise. This was not observed with ($P_d=5$).

FIG. 9 shows the daily errors in the MDI therapy parameters estimates, defined as $$100\frac{(x_d - x^{opt})}{x^{opt}},$$

where $X^{opt}$ is the optimal therapy parameter and $X_d$ is the daily parameter. Positive and negative errors, indicating overestimation and underestimation, respectively, of each MDI therapy parameter are grouped together for better visualization of convergence. the present algorithm was able to reduce the initial error created in day 1 for the four therapy parameters, as opposite to the baseline R2R. Furthermore, it was observed that both lunch and dinner carbohydrate ratios converged to values smaller than the theoretical optimal value. This is justified since the VP consumed snacks in the afternoon and bedtime. the present algorithm successfully adjusted for the extra carbohydrates by decreasing the carbohydrate ratio.

Changing the basal dose (note that equation (10) imposes a change in basal rate if glucose levels are increasing, not if they are high). Even though it is possible to correct high glucose levels by increasing the basal dose, the risk of hypoglycemia will increase for nights where glucose is stable but at normal levels.

Real-world data often contain multiple consecutive meals and insulin boluses, which may result in the lack of practical identifiability. In an ideal system-identification experiment, parameters should be identified using uncorrelated inputs. In the present case, this can be achieved by exciting only one channel at a time (meal, bolus, or basal channels). Since this is rarely the case in real life, the following measures to cope with this identifiability problem were applied: (i) the use of prior distributions to regulate parameter estimates, and (ii) the use of parameter sensitivities in the update rules of the MDI therapy parameters. A truncated prior distribution was employed to guaranty that the posterior distribution is bounded. Yet these constraints were chosen large enough to let the data drive the parameter estimates. The estimation of physiologically plausible parameters and the convergence of the algorithm in simulation validates the efficacy of these measures.

In principle, the present algorithm can be used to optimize therapy parameters for pump users. However, the identifiability issue becomes more apparent in the estimation process of pump therapy parameters compared to MDI therapy parameters. This is because pump users adjust multiple basal insulin values during the day with the aim of accommodating diurnal insulin sensitivity changes. This is a limiting factor, from an estimation problem point of view, since multiple model parameters would affect the same part of the day (for example, lunch carbohydrate ratio and afternoon basal rate). For closed-loop insulin delivery systems (artificial pancreas systems) where insulin delivery is automatically adjusted around usual basal rates, adjusting only one average basal rate (implemented throughout the day) might solve this identifiability issue.

A trait of the present algorithm is how the gain (learning rate) of the run-to-run control law is adapted depending on the quality of the data, the goodness of fit, and the sensitivities of the estimated MDI therapy parameters. For instance, when the algorithm is run with low-quality data such as those resulting from correlated inputs, the estimated parameters will be correlated which will result in higher sensitivities and consequently a lower learning rate. Similarly, in the presence of unknown events (such as physical activities or non-recorded meals), the goodness of fit is reduced resulting in a lowering of the learning rate. The adapted learning rate is high only when the MDI therapy parameters are estimated with low sensitivities and the model fits the data with a small mean absolute error.

The simulations were designed to challenge the present model-based algorithm by (i) providing wrong inputs to the model, mainly not entering the two daily snacks and simulating carbohydrate counting errors, (ii) simulating random glucose, meal, and insulin fluxes that the present model is unable to explain.

These challenges led to an increased coefficient of variation of the parameter estimates and worsening of the model fit. Despite these challenging simulations, there was an improvement in the time spent in target and the time spent in hypoglycemia. Regardless, this simulation environment does not consider all perturbations and variabilities which precludes the generalization of these results.

In the baseline R2R, each therapy parameter is updated to optimize a glycemic outcome (for example: time spent in hypoglycemia after lunch, or average night glucose); therefore, it was not possible to converge in situations where both errors in basal insulin dose and carbohydrate ratios were positive (FIG. 9). This resulted on not improving hypoglycemia during night. In fact, the classical R2R formulation does not consider correlations between changing a basal insulin dose and changing a carbohydrate ratio. In the present method, this correlation is inherently considered since optimal therapy parameters are estimated simultaneously by fitting the data.

In simulation, day-to-day variability due to unusual days of sickness, high stress, or large carbohydrate counting errors, may result in small oscillations in the MDI therapy parameters recommendations. This problem was avoided by averaging recommendations from multiple days. Note that in the simulation $P_d=5$, however in real-life this value should be at least bigger than 7 days to consider small differences between week days.

It will be appreciated that not all technical effects mentioned herein need to be enjoyed in each and every embodiment of the present technology. For example, one or more embodiments of the present technology may be implemented without the user enjoying some of these technical effects, while other non-limiting embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fiber-optic connection), electronic means (such as using wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting.

What is claimed is:

1. A method for determining recommended multiple daily injection (MDI) therapy values for administering to a given subject, the method being executed by at least one processor, the at least one processor being operatively connected to an artificial pancreas system comprising a continuous glucose monitor (CGM) and an infusion pump, the method comprising:
receiving data values relating to a consumed meal by the given subject, an insulin basal dose administered to the given subject, and an insulin bolus dose administered to the given subject;
receiving an initial meal ratio parameter and an initial basal insulin dose used by the given subject;
predicting, using a computer model of the glucoregulatory system of the given subject based on the data values relating to the consumed meal by the given subject, the insulin basal dose, the insulin bolus dose, and the initial meal ratio parameter, a predicted glucose concentration parameter representative of predicted blood glucose concentration of the given subject after the consumed meal and administration of the insulin bolus dose and the insulin basal dose;
receiving, from the CGM of the artificial pancreas system, an actual glucose concentration parameter representative of an actual blood glucose concentration measurement of the given patient;
estimating, by a run-to-run (R2R) control algorithm using the computer model of the glucoregulatory system of the given subject based on the predicted glucose con-

37 centration parameter and the actual glucose concentration parameter, a set of optimal MDI therapy parameters; and determining, based on the set of optimal MDI therapy parameters, a set of recommended MDI therapy parameters, the set of recommended MDI therapy parameters comprising an optimal meal ratio parameter to be consumed by the subject, and an optimal basal insulin dose to be administered to the given subject;

outputting the set of recommended MDI therapy parameters to the subject; and transmitting, to the artificial pancreas system, a control command to cause the infusion pump to inject the optimal basal insulin dose to the subject.

2. The method of claim 1, wherein the method further comprises, prior to said predicting, using the computer model of the glucoregulatory system of the given subject, the predicted glucose concentration parameter:

determining, based on the consumed meal, a rate of meal glucose appearance;

determining, based on the insulin basal dose and an initial optimal basal insulin dose, a first rate of insulin appearance in response to the insulin basal dose;

determining, based on the meal ratio parameter and the insulin bolus dose, a second rate of insulin appearance in response to the insulin bolus dose; and wherein said determining the glucose concentration parameter is further based on: the rate of meal glucose appearance, the first rate of insulin appurtenance, and the second rate of insulin appearance.

3. The method of claim 2, wherein said estimating the set of optimal MDI therapy parameters comprises:

initializing a set of model parameters; and determining a set of model parameters estimates, the set of model parameters estimates comprising the set of optimal MDI therapy parameters, said determining being based on:

the set of model parameters, the predicted glucose concentration parameter, the actual glucose concentration parameter, and the data values relating to the consumed meal by the given subject, the insulin basal dose, the insulin bolus dose, and the initial meal ratio parameter.

4. The method of claim 1, wherein said predicting, using the computer model of the glucoregulatory system of the given subject, the predicted glucose concentration parameter is further based on: an insulin sensitivity, a time-to-peak (TTP) of insulin action, a carbohydrate sensitivity, and a TTP of carbohydrate absorption.

5. The method of claim 1, wherein said estimating by the run-to-run (R2R) control algorithm using the computer model of the glucoregulatory system of the given subject is performed using a gradient descent optimization, and a Monte-Carlo Markov Chain (MCMC) sampling.

6. The method of claim 1, wherein the data values relating to the consumed meal comprises an estimated weight of carbohydrates in the meal, the optimal meal ratio is a carbohydrate ratio for pre-meal glucose values, and the glucose concentration parameter is an interstitial glucose concentration.

7. The method of claim 1, wherein said estimating by the run-to-run (R2R) control algorithm using the computer model of the glucoregulatory system of the given subject comprises using a maximum a posteriori (MAP) estimate.

8. The method of claim 7, wherein the MAP estimate is obtained using:

38

$$p^* = \arg\max_p \mathcal{P}(p \mid Y_{1:N}, U_{1:N}) \Leftrightarrow p^* = \arg\max_p \mathcal{P}(Y_{1:N} \mid U_{1:N}, p)\mathcal{P}(p)$$

where $Y_{1:N}$ is the actual glucose concentration parameter $U_{1:N}$ is a set of inputs comprising the data values relating to the consumed meal by the given subject, the insulin basal dose, the insulin bolus dose, and the initial meal ratio parameter, p, is the set of model parameters.

9. The method of claim 1, further comprising, prior to said determining the set of recommended MDI therapy parameters:

determining a coefficient of variation (CV) of the set of MDI therapy parameters;

determining local mean absolute error (MAE) of the difference between the observed glucose levels and the predicted glucose resulting from the fit; and determining a learning rate coefficient based on the CV and the MAE; and wherein said determining the set of recommended MDI therapy parameters is further based on the learning rate coefficient.

10. The method of claim 9, further comprising, prior to said determining the set of recommended MDI therapy parameters:

determining a saturation function; and wherein said determining the set of recommended MDI therapy parameters is obtained using:

$$X_{d+1} = X_d + \phi(\eta(\mathbb{E}[\widehat{X_d}] - X_d))$$

where $X_{d+1}$ is the recommended set of MDI therapy parameters, $X_d$ is an initial set of therapy parameters, $\mathbb{E}[\widehat{X_d}]$ is the estimated optimal therapy parameter, $\eta$ is the learning rate and $\phi$ is the saturation function.

11. A system for determining recommended multiple daily injections (MDI) therapy values for administering to a given subject, the system comprising:

a processor;

a non-transitory computer-readable storage medium operatively connected to the processor, the computer-readable storage medium comprising instructions;

an input/output interface operatively connected to the processor;

the system being operatively connected to a continuous glucose monitor (CGM) and an infusion pump, the processor, upon executing the instructions, being configured for:

receiving data values relating to a consumed meal by the given subject, an insulin basal dose administered to the given subject, and an insulin bolus dose administered to the given subject;

receiving an initial meal ratio parameter and an initial basal insulin dose used by the given subject;

predicting, using a computer model of the glucoregulatory system of the given subject, based on data values relating to the consumed meal by the given subject, the insulin basal dose, the insulin bolus dose, and the initial meal ratio parameter, a predicted glucose concentration parameter representative of predicted blood glucose concentration of the given subject after the consumed meal and administration of the insulin bolus dose and the insulin basal dose;

receiving, from the CGM, an actual glucose concentration parameter representative of an actual blood glucose concentration measurement of the given subject;

estimating, by a run-to-run (R2R) control algorithm using the computer model of the glucoregulatory system of the given subject based on the predicted glucose concentration parameter and the actual glucose concentration parameter, a set of optimal MDI therapy parameters; and determining, based on the set of optimal MDI therapy parameters, a set of recommended MDI therapy parameters, the set of recommended MDI therapy parameters comprising an optimal meal ratio parameter to be consumed by the given subject, and an optimal basal insulin dose to be administered to the given subject;

outputting, to the input/output interface, the set of recommended MDI therapy parameters to the subject; and transmitting, to the artificial pancreas system, a control command to cause the infusion pump to inject the optimal basal insulin dose to the subject.

12. The system of claim 11, wherein the processor is further configured for, prior to the determining the predicted glucose concentration parameter:

determining, based on the data values relating to the consumed meal, a rate of meal glucose appearance;

determining, based on the insulin basal dose and an initial optimal basal insulin dose, a first rate of insulin appearance in response to the insulin basal dose;

determining, based on the meal ratio parameter and the insulin bolus dose, a second rate of insulin appearance in response to the insulin bolus dose; and wherein said predicting the glucose concentration parameter is further based on: the rate of meal glucose appearance, the first rate of insulin appurtenance, and the second rate of insulin appearance.

13. The system of claim 12, wherein said estimating by the run-to-run (R2R) control algorithm using the computer model of the glucoregulatory system of the given subject the set of optimal MDI therapy parameters comprises:

initializing a set of model parameters; and determining, a set of model parameters estimates, the set of model parameters estimates comprising the set of optimal MDI therapy parameters, said determining being based on:

the set of model parameters, the predicted glucose concentration parameter, the actual glucose concentration parameter, and the data values relating to the consumed meal by the given subject, the insulin basal dose, the insulin bolus dose, and the initial meal ratio parameter.

14. The system of claim 11, wherein said predicting using the computer model of the glucoregulatory system of the given subject, the predicted glucose concentration parameter is further based on: an insulin sensitivity, a time-to-peak (TTP) of insulin action, a carbohydrate sensitivity, and a TTP of carbohydrate absorption.

15. The system of claim 11, wherein said estimating is performed using a gradient descent optimization, and a Monte-Carlo Markov Chain (MCMC) sampling.

16. The system of claim 11, wherein the data values relating to the consumed meal comprises an estimated weight of carbohydrates in the meal, the optimal meal ratio is a carbohydrate ratio for pre-meal glucose values, and the glucose concentration parameter is an interstitial glucose concentration.

17. The system of claim 11, wherein said estimating by the run-to-run (R2R) control algorithm using the computer model of the glucoregulatory system of the given subject comprises using a maximum a posteriori (MAP) estimate.

18. The system of claim 17, wherein the MAP estimate is obtained using:

$$p^* = \arg\max_p \mathcal{P}(p \mid Y_{1:N}, U_{1:N}) \Leftrightarrow p^* = \arg\max_p \mathcal{P}(Y_{1:N} \mid U_{1:N}, p)\mathcal{P}(p)$$

where $Y_{1:N}$ is the actual glucose concentration parameter $U_{1:N}$ is a set of inputs comprising the data values relating to the consumed meal by the given subject, the insulin basal dose, the insulin bolus dose, and the initial meal ratio parameter, p, is the set of model parameters.

19. The system of claim 11, wherein the processor is further configured for, prior to said determining the set of recommended MDI therapy parameters:

determining a coefficient of variation (CV) of the set of MDI therapy parameters;

determining local mean absolute error (MAE) of the difference between the observed glucose levels and the predicted glucose resulting from the fit; and determining a learning rate coefficient based on the CV and the MAE; and wherein said determining the set of recommended MDI therapy parameters is further based on the learning rate coefficient.

20. The system of claim 19, wherein the processor is further configured for, prior to said determining the set of recommended MDI therapy parameters:

determining a saturation function; and wherein said determining the set of recommended MDI therapy parameters is obtained using:

$$X_{d+1} = X_d + \phi(\eta(\mathbb{E}[\widehat{X_d}] - X_d))$$

where $X_{d+1}$ is the recommended set of MDI therapy parameters, $X_d$ is an initial set of therapy parameters, $\mathbb{E}[\widehat{X_d}]$ is the estimated optimal therapy parameter, $\eta$ is the learning rate and $\phi$ is the saturation function.

* * * * *